United States Patent [19]
Pitzele et al.

[11] Patent Number: 6,114,381
[45] Date of Patent: Sep. 5, 2000

[54] NON-HETEROCYCLIC β-PHENYL-α-AMINOPROPIONIC ACID N-PHENYL AMIDES FOR TREATMENT OF NEUROTOXIC INJURY

[75] Inventors: Barnett S. Pitzele, Skokie; Nizal S. Chandrakumar, Vernon Hills; Michael Clare, Skokie, all of Ill.

[73] Assignee: G. D. Searle & Co., Chicago, Ill.

[21] Appl. No.: 09/170,784

[22] Filed: Oct. 13, 1998

Related U.S. Application Data

[62] Division of application No. 08/908,492, Aug. 7, 1997, abandoned, which is a continuation of application No. 08/153,393, Nov. 16, 1993, abandoned, which is a continuation of application No. 07/810,620, Dec. 19, 1991, abandoned.

[51] Int. Cl.[7] ............... A61K 31/275; A61K 31/165; C07C 229/36; C07C 233/04
[52] U.S. Cl. ............... 514/522; 560/27; 560/37; 564/157; 564/182; 514/563; 514/616; 514/620; 558/414
[58] Field of Search ............... 558/414; 564/157, 564/182; 560/27, 37; 514/522, 620, 563, 616

[56] References Cited

U.S. PATENT DOCUMENTS 4,695,580  9/1987  Ohashi et al. ............... 514/412

FOREIGN PATENT DOCUMENTS 19612828  2/1997  Germany.

*Primary Examiner*—Joseph McKane
*Assistant Examiner*—Ebenezer Sackey
*Attorney, Agent, or Firm*—J. Timothy Keane

[57] ABSTRACT

Compounds, compositions and methods of treatment are described to control brain damage associated with anoxia or ischemia which typically follows stroke, cardiac arrest or perinatal asphyxia. The treatment includes administration of a β-phenyl-α-aminopropionic acid N phenyl amide compound as an antagonist to inhibit excitotoxic actions at major neuronal excitatory amino acid receptor sites. Compounds of most interest are those of the formula

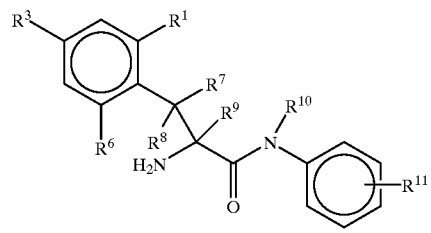

wherein each of $R^1$ and $R^5$ is independently selected from hydrido, fluoro, chloro, bromo, methyl and ethyl; wherein $R^3$ is selected from hydroxy, methoxy, ethoxy, methoxycarbonyloxy, ethoxycarbonyloxy, (2-methylpropoxy)carbonyloxy and (2-propenyloxy) carbonyloxy; wherein each of $R^6$, $R^7$ and $R^8$ is hydrido; wherein each of $R^9$ and $R^{10}$ is independently selected from hydrido, methyl and ethyl; wherein $R^{11}$ is one or more groups independently selected from hydrido, fluoro, chloro, hydroxy, methoxy, methyl and ethyl; or a tautomer or enantiomer therefor, or a pharmaceutically-acceptable salt or ester thereof.

24 Claims, No Drawings

NON-HETEROCYCLIC β-PHENYL-α-AMINOPROPIONIC ACID N-PHENYL AMIDES FOR TREATMENT OF NEUROTOXIC INJURY

This application is a divisional of Ser. No. 08/908,492 filed Aug. 7, 1997 now abandoned, which is a continuation of Ser. No. 08/153,393 filed Nov. 16, 1993 now abandoned, which is a continuation of Ser. No. 07/810,620 filed Dec. 19, 1991 now abandoned.

FIELD OF THE INVENTION

This invention is in the field of clinical neurology and relates specifically to compounds, compositions and methods for neuroprotective purposes such as controlling brain damage which occurs during periods of anoxia or ischemia associated with stroke, cardiac arrest or perinatal asphyxia.

BACKGROUND OF THE INVENTION

Unlike other tissue which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which was early characterized as a fast excitatory transmitter in the mammalian brain. Glutamate is also known as a powerful neurotoxin capable of killing CNS neurons under certain pathological conditions which accompany stoke and cardiac arrest. Normal glutamate concentrations are maintained within brain tissue by energy-consuming transport systems. Under low energy conditions which occur during periods of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either interfering with synaptic transmission through blockade of the sodium or calcium ion channel or by the specific antagonism of postsynaptic glutamate receptors [see S. M. Rothman and J. W. Olney. "Glutamate and the Pathophysiology of Hypoxia—Ischemic Brain Damage," *Annals of Neurology*, 19, No. 2 (1986)]. Glutamate is characterized as a broad spectrum agonist having activity at three neuronal excitatory amino acid receptor sites. These receptor sites are named after the amino acids which selectively excite them, namely: kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia, or ischemia caused by stroke, cardiac arrest or perinatal asphyxia.

Phencyclidine (PCP) and the PCP-like compound ketamine have been found to reduce selectively the excitatory effects of NMDA as compared to KA and QUIS [Anis, N. A. et al, "The Dissociative Anaesthetics, Ketamine and Phencyclidine, Selectively Reduce Excitation of Central Mammalian Neurones by N-Methyl-Aspartate", *Br. J. Pharmacol.*, 79, 565 (1983)]. Other compounds having PCP-like properties such as cyclazocine, kynurenate and various barbiturates such as secobarbital, amobarbital and pentobarbital, have been tested as antagonists in blocking NMDA- or KA-induced neurotoxicity [J. W. Olney et al., "The Anti-Excitotoxic Effects of Certain Anesthetics, Analgesics and Sedative-Hypnotics," *Neuroscience Letters*, 68, 29–34 (1986)].

A correlation has been found between the PCP binding effects of some PCP-derivative stereoisomers and NMDA antagonism. For example, the stereoselective effects of cis-N-(1-phenyl-4-methylcyclohexyl)piperidine and (+)-1-(1-phenylcyclohexyl)-3-methylpiperidine[(+)-PCMP] over each of their corresponding isomer counterparts in reducing the excitatory action of NMDA have been confirmed in binding and behavioral data [S. D. Berry et al, "Stereoselective Effects of Two Phencyclidine Derivatives on N-Methylaspartate Excitation of Spinal Neurones in the Cat and Rat", *Eur. J. Pharm.*, 96, 261–267 (1983)]. Also, the compound (+)-PCMP has been found to be a potent inhibitor of the specific binding of [$^3$H]PCP to rat cerebral cortical membranes [M. E. Goldman et al, "Differentiation of [$^3$H] Phencyclidine and (+)-[$^3$H]SKF-10,047 Binding Sites in Rat Cerebral Cortex", *FEBS Lett.*, 170, 333–336 (1985)].

Other neurochemical mechanisms by which PCP alters behavior are known. For example, binding assays of the PCP/sigma site have been used to evaluate arylcycloalkylamines [R. Quirion, "Phencyclidine (Angel Dust)/Sigma 'Opiate' Receptor: Visualization by Tritium-Sensitive Film", *Proc. Natl. Acad. Sci. U.S.A.*, 78, 5881 (1981)]. PCP-like drugs may induce ipsilateral turning in rats by action on the PCP/sigma receptor as indicated by studies with arylcycloalkylamines, sigma-agonist benzomorphans and 1,3-dioxolanes.

These PCP-like classes of compounds have been found to inhibit NMDA-induced acetylcholine (ACh) release and such ACh release has been correlated with their affinity for the PCP receptor and with behavioral activity (L. D. Snell et al, "Antagonism of N-Methyl-D-Aspartate-Induced Transmitter Release in the Rat Striatum by Phencyclidine-Like Drugs and its Relationship to Turning Behavior", *J. Pharmacol. Exp. Ther.*, 235, No. 1, 50–56 (1985)].

Certain β-phenyl-α-aminopropionic acid N-phenylamide derivatives are known for various pharmaceutical purposes. For example, Japanese Patent Kokai No. 61-145,148 published Jul. 2, 1986 describes (3,4-dihydroxyphenyl)serine derivatives for use as antiallergic and antiinflammatory agents for prophylaxis and treatment of heart and brain diseases caused by ischemia. German Offen. 2,156,835 published May 25, 1972 describes the compound 4-[[2-(benzoylamino)-3-(4-hydroxyphenyl)-1-oxopropyl] methylamino-(S)-benzoic acid for in vitro and in vivo testing of pancreatic enzyme sufficiency.

Polycyclohetero-containing β-phenyl-α-aminopropionic acid N-phenylamide derivatives are known to have pharmaceutical uses. For example, a family of aminoacylcarbazole derivatives, including 9-(2-amino-1-oxo-3-phenylpropyl)-9H-carbazole, has been synthesized and evaluated for antimicrobial acitivity [A. M. El-Nagger et al, *J. Heterocycl. Chem.*, 19(5), 1025–1028 (1982)

DESCRIPTION OF INVENTION

Control of neuropathological processes and the neurodegenerative consequences thereof in mammals is provided by treating a mammal susceptible to neurotoxic injury with an anti-excitotoxic amount of a compound of a class of β-phenyl-α-aminopropionic acid N-phenylamide derivatives represented by Formula I:

(I)

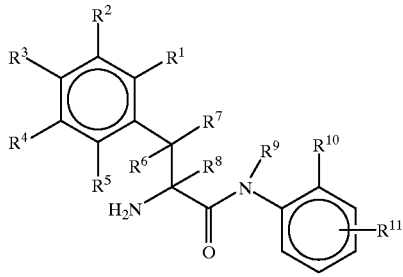

wherein each of $R^1$, $R^2$, $R^4$, $R^5$, $R^6$, $R^7$, $R^8$, and $R^{11}$ is independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, alkanoyl and amino and amido radicals of the formula

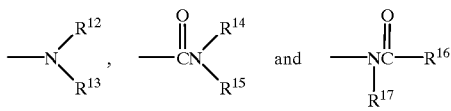

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, aralkyl and aryl;

wherein $R^3$ is selected from hydrido, hydroxy, alkyl, cycloalkyl, cycloalkylalkyl, haloalkyl, aryl, aralkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, aryl, aralkyl, hydroxyalkyl, alkoxyalkyl, alkoxycarbonyl and alkanoyl;

wherein $R^9$ and $R^{10}$ may be taken together to form an alkylene chain or alkenylene chain having two to about ten carbon atoms in said alkylene or alkenylene chain, and to which chain may be fused a carbocyclic ring, said carbocyclic ring being selected from saturated, partially unsaturated and fully unsaturated rings having three to about eight ring carbon atoms; wherein $R^{10}$ and $R^{11}$ may be taken together to form a fused aromatic ring; and wherein any of said alkylene chain, said alkenylene chain, said carbocyclic ring and said fused aromatic ring may be substituted at a substitutable position with one or more groups selected from alkyl, cycloalkyl, cycloalkylalkyl, carboxyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, alkanoyl, mercapto, alkylthio, arylthio, alkylsulfinyl, arylsulfinyl, alkylsulfonyl, arylsulfonyl, and amino and amido radicals of the formula

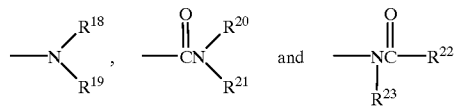

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, aralkyl and aryl;

with the proviso that at least one of $R^2$, $R^3$ and $R^4$ must be a group other than hydrido;

or a tautomer or an enantiomer thereof, or a pharmaceutically-acceptable ester or salt thereof.

A preferred class of compounds consists of those compounds of Formula I wherein each of $R^1$, $R^2$, $R^4$, $R^5$, $R^6$, $R^7$, $R^8$ and $R^{11}$ is independently selected from hydrido, alkyl, cycloalkyl, cycloalkylalkyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, alkanoyl, and amino and amido radicals of the formula

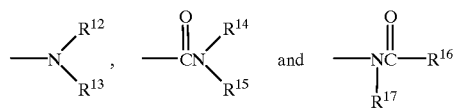

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, phenalkyl and phenyl;

wherein $R^3$ is selected from hydrido, hydroxy, alkyl, cycloalkyl, cycloalkylalkyl, haloalkyl, phenyl, phenalkyl, hydroxyalkyl, alkoxyalkyl, alkoxycarbonyl alkenylalkyloxycarbonyloxy, alkoxycarbonyloxy, acyl and alkanoyl;

wherein $R^9$ is selected from alkyl, cycloalkyl, cycloalkylalkyl, haloalkyl, phenyl, phenalkyl, hydroxyalkyl and alkoxyalkyl;

wherein $R^9$ and $R^{10}$ may be taken together to form an alkylene chain or alkenylene chain having two to about ten carbon atoms in said alkylene or alkenylene chain, and to which chain may be fused a carbocyclic ring, said carbocyclic ring being selected from saturated, partially unsaturated and fully unsaturated rings having three to about eight ring carbon atoms; wherein $R^{10}$ and $R^{11}$ may be taken together to form a fused aromatic ring; and wherein any of said alkylene chain, said alkenylene chain, said carbocyclic ring and said fused aromatic ring may be substituted at a substitutable position with one or more groups selected from alkyl, cycloalkyl, cycloalkylalkyl, carboxyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, cyano, cyanoamino, alkanoyl, and amino and amido radicals of the formula

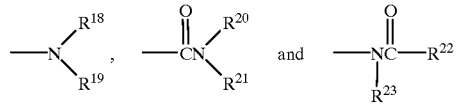

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, phenalkyl and phenyl;

with the proviso that at least one of $R^2$, $R^3$ and $R^4$ must be a group other than hydrido;

or a tautomer or an enantiomer thereof, or a pharmaceutically-acceptable ester or salt thereof.

A more preferred class of compounds consists of those compounds of Formula I wherein each of $R^1$, $R^2$, $R^4$, $R^5$, $R^6$, $R^7$, $R^8$ and $R^9$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

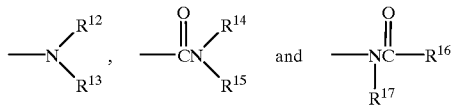

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydrido, hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, hydroxyalkyl and alkoxyalkyl;

wherein $R^9$ and $R^{10}$ may be taken together to form an alkylene chain or alkenylene chain having two to about ten carbon atoms in said alkylene or alkenylene chain, and to which chain may be fused a said carbocyclic ring being selected from saturated, partially unsaturated and fully unsaturated rings having three to about eight ring carbon atoms; wherein $R^8$ and $R^9$ may be taken together to form a fused aromatic ring; and wherein any of said alkylene chain, said alkenylene chain, said carbocyclic ring and said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl and amino and amido radicals of the formula

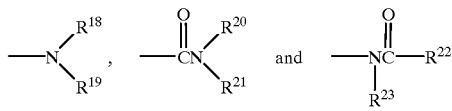

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

with the proviso that at least one of $R^2$, $R^3$ and $R^4$ must be a group other than hydrido;

or a tautomer or an enantiomer thereof, or a pharmaceutically-acceptable ester or salt thereof.

It is believed that compounds defined by Formula I are novel when the defined family is qualified with the proviso requirement that at least one of $R^2$, $R^3$ and $R^4$ be a group other than hydrido. However, the described utility for compounds of Formula I is believed novel for all compounds within Formula I without the proviso requirement. Accordingly, the use of such compounds would be novel in methods to mediate neuropathological processes and the neurodegenerative consequences thereof, such as methods to treat a subject susceptible to or afflicted with a neurotoxic injury.

A first sub-class of more preferred compounds within Formula I consists of compounds of Formula II:

(II)

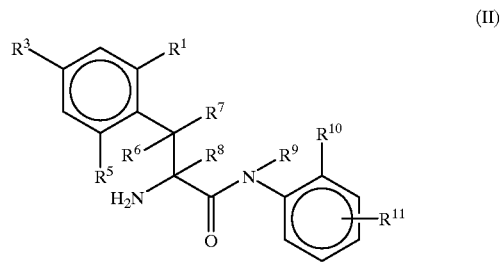

wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

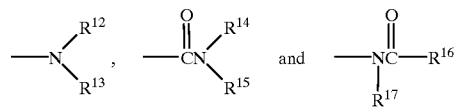

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^7$ is selected from alkyl, cycloalkyl, cycloalkylalkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

wherein $R^{10}$ and $R^{11}$ may be taken together to form a fused aromatic ring; wherein said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl, and amino and amido radicals of the formula

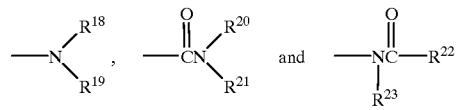

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

More preferred compounds within the first sub-class of compounds defined by Formula II are those compounds wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy and alkoxyalkyl;

wherein R³ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein each of R⁶, R⁷ and R⁸ is independently selected from hydrido, alkyl, haloalkyl, hydroxyalkyl and alkoxyalkyl;

wherein R⁹ is selected from alkyl, cycloalkyl, cycloalkylalkyl, haloalkyl, hydroxyalkyl and alkoxyalkyl;

or a tautomer or enantiomer thereof, or a pharmaceutically-acceptable ester or salt thereof.

Even more preferred compounds within the first sub-class of compounds defined by Formula II are those compounds wherein each of R¹, R⁵, R¹⁰ and R¹¹ is independently selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxymethyl, hydroxyethyl, hydroxypropyl, methoxy, ethoxy, propoxy, methoxymethyl, ethoxymethyl and ethoxyethyl;

wherein R³ is selected from hydroxy, methoxy, ethoxy, methoxycarbonyloxy, ethoxycarbonyloxy, (2-methylpropoxy)carbonyloxy and (2-propenyloxy) carbonyloxy;

wherein each of R⁶, R⁷ and R⁸ is hydrido;

R⁹ is selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, hydroxyethyl, hydroxypropyl and ethoxyethyl;

or a tautomer or an enantiomer thereof, or a pharmaceutically-acceptable ester or salt thereof.

A family of highly preferred compounds within Formula II consists of compounds, and tautomers and enantiomers thereof, as well as the pharmaceutically-acceptable salts and esters thereof, as follows:

αS-amino-4-hydroxy-N,2,6-trimethyl-N-phenylbenzenepropanamide;
αS-amino-2-chloro-4-hydroxy-N,6-dimethyl-N-phenylbenzenepropanamide;
αS-amino-2-bromo-4-hydroxy-N,6-dimethyl-N-phenylbenzenepropanamide;
αS-amino-4-methoxy-N,2,6-trimethyl-N-phenylbenzenepropanamide;
αS-amino-2-chloro-4-methoxy-N,6-dimethyl-N-phenylbenzenepropanamide;
αS-amino-2-bromo-4-methoxy-N,6-dimethyl-N-phenylbenzenepropanamide;
αS-amino-4-(methoxycarbonyl)oxy-N,2,6-trimethyl-N-phenylbenzenepropanamide;
αS-amino-2-chloro-4-(methoxycarbonyl)oxy-N,6-dimethyl-N-phenylbenzene-propanamide;
αS-amino-2-bromo-4-(methoxycarbonyl)oxy-N,6-dimethyl-N-phenylbenzene-propanamide;
αS-amino-4-(ethoxycarbonyl)oxy-N,2,6-trimethyl-N-phenylbenzenepropanamide;
αS-amino-2-chloro-4-(ethoxycarbonyl)oxy-N,6-dimethyl-N-phenylbenzene-propanamide;
αS-amino-2-bromo-4-(ethoxycarbonyl)oxy-N,6-dimethyl-N-phenylbenzene-propanamide;
αS-amino-4-((2-methylpropoxy)carbonyl)oxy-N,2,6-trimethyl-N-phenylbenzenepropanamide;
αS-amino-2-chloro-4-((2-methylpropoxy)carbonyl)oxy-N,6-dimethyl-N-phenylbenzene-propanamide;
αS-amino-2-bromo-4-((2-methylpropoxy)carbonyl)oxy-N,6-dimethyl-N-phenylbenzene-propanamide;
αS-amino-4-((2-propenyloxy)carbonyl)oxy-N,2,6-trimethyl-N-phenylbenzenepropanamide;
αS-amino-2-chloro-4-((2-propenyloxy)carbonyl)oxy-N,6-dimethyl-N-phenylbenzene-propanamide;
αS-amino-2-bromo-4-((2-propenyloxy)carbonyl)oxy-N,6-dimethyl-N-phenylbenzene-propanamide;
αR-amino-4-hydroxy-N,2,6-trimethyl-N-phenylbenzenepropanamide;
αR-amino-2-chloro-4-hydroxy-N,6-dimethyl-N-phenylbenzenepropanamide;
αR-amino-2-bromo-4-hydroxy-N,6-dimethyl-N-phenylbenzenepropanamide;
αR-amino-4-methoxy-N,2,6-trimethyl-N-phenylbenzenepropanamide;
αR-amino-2-chloro-4-methoxy-N,6-dimethyl-N-phenylbenzenepropanamide;
αR-amino-2-bromo-4-methoxy-N,6-dimethyl-N-phenylbenzenepropanamide;
αR-amino-4-(methoxycarbonyl)oxy-N,2,6-trimethyl-N-phenylbenzenepropanamide;
αR-amino-2-chloro-4-(methoxycarbonyl)oxy-N,6-dimethyl-N-phenylbenzene-propanamide;
αR-amino-2-bromo-4-(methoxycarbonyl)oxy-N,6-dimethyl-N-phenylbenzene-propanamide;
αR-amino-4-(ethoxycarbonyl)oxy-N,2,6-trimethyl-N-phenylbenzenepropanamide;
αR-amino-2-chloro-4-(ethoxycarbonyl)oxy-N,6-dimethyl-N-phenylbenzene-propanamide;
αR-amino-2-bromo-4-(ethoxycarbonyl)oxy-N,6-dimethyl-N-phenylbenzene-propanamide;
αR-amino-4-((2-methylpropoxy)carbonyl)oxy-N,2,6-trimethyl-N-phenylbenzenepropanamide;
αR-amino-2-chloro-4-((2-methylpropoxy)carbonyl)oxy-N,6-dimethyl-N-phenylbenzene-propanamide;
αR-amino-2-bromo-4-((2-methylpropoxy)carbonyl)oxy-N,6-dimethyl-N-phenylbenzene-propanamide;
αR-amino-4-((2-propenyloxy)carbonyl)oxy-N,2,6-trimethyl-N-phenylbenzenepropanamide;
αR-amino-2-chloro-4-((2-propenyloxy)carbonyl)oxy-N,6-dimethyl-N-phenylbenzene-propanamide;
αR-amino-2-bromo-4-((2-propenyloxy)carbonyl)oxy-N,6-dimethyl-N-phenylbenzene-propanamide;

A second sub-class of more preferred compounds within Formula I consists of compounds of Formula III:

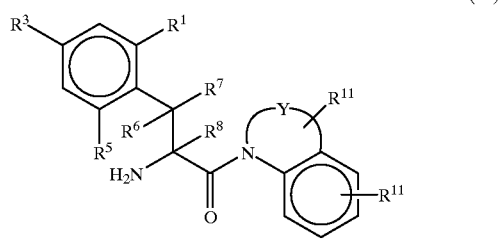

(III)

wherein each R¹¹ represents one or more groups and wherein each of R¹, R⁵ and R¹¹ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

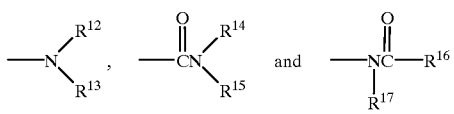

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein each of $R^6$, $R^7$ and $R^8$ is hydrido;

wherein Y is selected from one or more alkylene and alkenylene radicals of the formula

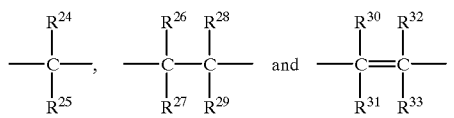

wherein each of $R^{24}$, $R^{25}$, $R^{26}$, $R^{27}$, $R^{28}$ and $R^{29}$ is independently selected from hydrido, alkyl, cycloalkyl, halo, haloalkyl, hydroxy, hydroxyalkyl, alkoxy, alkoxyalkyl, alkanoyl, and amino and amido radicals of the formula

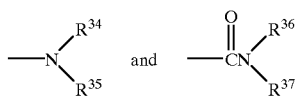

wherein each of $R^{34}$, $R^{35}$, $R^{36}$ and $R^{37}$ is independently selected from hydrido and alkyl; wherein $R^{24}$ and $R^{25}$ may be taken together to form oxo; wherein each of $R^{30}$, $R^{31}$, $R^{32}$ and $R^{33}$ is independently selected from hydrido, alkyl, haloalkyl, hydroxyalkyl and alkoxyalkyl;

wherein $R^{26}$ and $R^{28}$ may be taken together to form a saturated or partially unsaturated ring system having three to about ten ring carbon atoms; wherein $R^{30}$ and $R^{32}$ may be taken together to form a partially unsaturated or fully unsaturated ring system having three to about ten ring carbon atoms; wherein any of said saturated, partially unsaturated and fully unsaturated ring systems may be substituted at a substitutable position with one or more groups selected from alkyl, cycloalkyl, cycloalkylalkyl, carboxyl, haloalkyl, hydroxy, hydroxyalkyl, alkoxy, alkoxyalkyl, alkoxycarbonyl, and amino and amido radicals of the formula

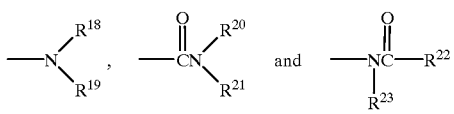

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

More preferred compounds within the second sub-class of compounds defined by Formula III are those compounds wherein each of $R^1$, $R^5$ and $R^{11}$ is independently selected from hydrido, halo, alkyl, cycloalkyl, cycloalkylalkyl, haloalkyl, hydroxy, hydroxyalkyl, alkoxy and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^{26}$ and $R^{28}$ may be taken together to form a saturated or partially unsaturated ring system having three to about eight ring carbon atoms; wherein $R^{30}$ and $R^{32}$ may be taken together to form a partially unsaturated or fully unsaturated ring system having three to about eight ring carbon atoms; and wherein any of said saturated, partially unsaturated and fully unsaturated ring systems may be substituted at a substitutable position with one or more groups selected from alkyl, cycloalkyl, cycloalkylalkyl, carboxyl, haloalkyl, hydroxy, hydroxyalkyl, alkoxy and alkoxyalkyl;

or a tautomer or enantiomer thereof, or a pharmaceutically-acceptable salt or ester thereof.

Even more preferred compounds within the second sub-class of compounds defined by Formula III are those compounds wherein each of $R^1$, $R^5$ and $R^{11}$ is independently selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxymethyl, hydroxyethyl, hydroxypropyl, methoxy, ethoxy, propoxy, methoxymethyl, ethoxymethyl and ethoxyethyl; wherein $R^3$ is selected from hydroxy, methoxy, ethoxy, methoxycarbonyloxy, ethoxycarbonyloxy, (2-methylpropoxy)carbonyloxy and (2-propenyloxy)carbonyloxy; wherein Y together with the Formula III phenyl ring attached to Y forms a polycyclic group selected from

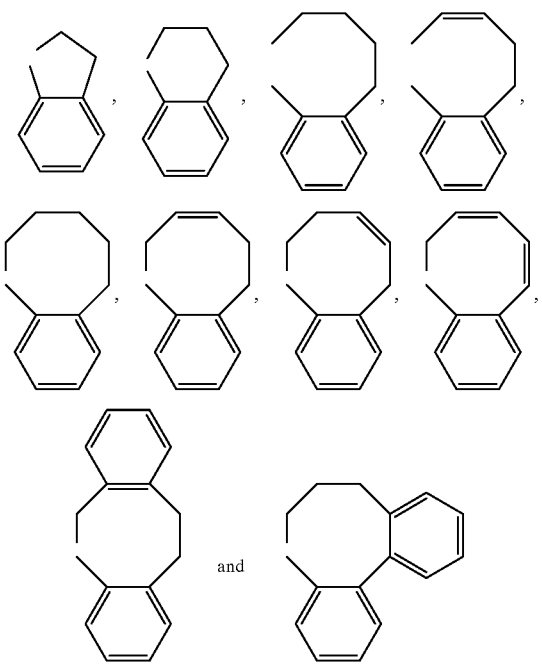

wherein any of said polycyclic groups may be substituted at a substitutable position with one or more groups selected from methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxy-methyl, hydroxyethyl, hydroxypropyl, methoxy, ethoxy, propoxy, methoxymethyl, ethoxymethyl and ethoxyethyl;

or a tautomer or enantiomer thereof, or a pharmaceutically-acceptable ester or salt thereof.

Even more highly preferred compounds within the second sub-class of compounds defined by Formula III are compounds of Formula IV:

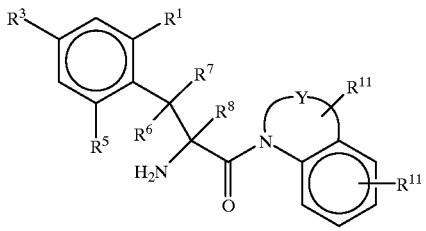

(IV)

wherein each of $R^1$ and $R^5$ is independently selected from hydrido, fluoro, chloro, bromo, methyl and ethyl; wherein $R^3$ is selected from hydroxy, methoxy, ethoxy, methoxycarbonyloxy, ethoxycarbonyloxy, (2-methylpropoxy)carbonyloxy and (2-propenyloxy) carbonyloxy; wherein each of $R^6$, $R^7$ and $R^8$ is hydrido; wherein Y is selected from —CH$_2$—CH$_2$— and —CH$_2$CH$_2$CH$_2$—; wherein each $R^{11}$ is one or more groups independently selected from hydrido, fluoro, chloro, hydroxy, methoxy, methyl and ethyl; or a tautomer or enantiomer thereof, or a pharmaceutically-acceptable salt or ester thereof.

A family of highly preferred specific compounds within Formula IV consists of compounds, and tautomers and enantiomers thereof, as well as the pharmaceutically-acceptable salts and esters thereof, as follows:

1-[2S-amino-3-(4-hydroxy-2,6-dimethylphenyl)-1-oxopropyl]-1,2,3,4-tetrahydro-3-methylquinoline;

1-[2S-amino-3-(4-hydroxy-2,6-dimethylphenyl)-1-oxopropyl]-2,3-dihydro-1H-indole;

1-[2S-amino-3-(4-hydroxy-2,6-dimethylphenyl)-1-oxopropyl]-1,2,3,4-tetrahydro-6-methoxyquinoline;

1-[2S-amino-3-(4-methoxy-2,6-dimethylphenyl)-1-oxopropyl]-1,2,3,4-tetrahydro-3-methylquinoline;

1-[(2S-amino-3-(4-methoxy-2,6-dimethylphenyl)-1-oxopropyl]-2,3-dihydro-1H-indole;

1-[2S-amino-3-(4-methoxy-2,6-dimethylphenyl)-1-oxopropyl]-1,2,3,4-tetrahydro-6-methoxyquinoline;

1-[2S-amino-3-(4-(methoxycarbonyl)oxy-2,6-dimethylphenyl)-1-oxopropyl]-1,2,3,4-tetrahydro-3-methylquinoline;

1-[2S-amino-3-(4-(methoxycarbonyl)oxy-2,6-dimethylphenyl)-1-oxopropyl]-2,3-dihydro-1H-indole;

1-[2S-amino-3-(4-(methoxycarbonyl)oxy-2,6-dimethylphenyl)-1-oxopropyl]-1,2,3,4-tetrahydro-6-methoxyquinoline;

1-[2S-amino-3-(4-(ethoxycarbonyl)oxy-2,6-dimethylphenyl)-1-oxopropyl]-1,2,3,4-tetrahydro-3-methylquinoline;

1-[2S-amino-3-(4-(ethoxycarbonyl)oxy-2,6-dimethylphenyl)-1-oxopropyl]-2,3-dihydro-1H-indole;

1-[2S-amino-3-(4-(ethoxycarbonyl)oxy-2,6-dimethylphenyl)-1-oxopropyl]-1,2,3,4-tetrahydro-6-methoxyquinoline;

1-[2S-amino-3-(4-((2-methylpropoxy)carbonyl)oxy-2,6-dimethylphenyl)-1-oxopropyl]-1,2,3,4-tetrahydro-3-methylquinoline;

1-[2S-amino-3-(4-((2-methylpropoxy)carbonyl)oxy-2,6-dimethylphenyl)-1-oxopropyl]-2,3-dihydro-1H-indole;

1-[2S-amino-3-(4-((2-methylpropoxy)carbonyl)oxy-2,6-dimethylphenyl)-1-oxopropyl]-1,2,3,4-tetrahydro-6-methoxyquinoline;

1-[2S-amino-3-(4-((2-propenyloxy)carbonyl)oxy-2,6-dimethylphenyl)-1-oxopropyl]-1,2,3,4-tetrahydro-3-methylquinoline;

1-[2S-amino-3-(4-((2-propenyloxy)carbonyl)oxy-2,6-dimethylphenyl)-1-oxopropyl]-2,3-dihydro-1H-indole;

1-(2S-amino-3-(4-((2-propenyloxy)carbonyl)oxy-2,6-dimethylphenyl)-1-oxopropyl]-1,2,3,4-tetrahydro-6-methoxyquinoline;

1-[2S-amino-3-(4-hydroxy-2-bromo-6-methylphenyl)-1-oxopropyl]-1,2,3,4-tetrahydro-3-methylquinoline;

1-[2S-amino-3-(4-hydroxy-2-bromo-6-methylphenyl)-1-oxopropyl]-2,3-dihydro-1H-indole;

1-[2S-amino-3-(4-hydroxy-2-bromo-6-methylphenyl)-1-oxopropyl]-1,2,3,4-tetrahydro-6-methoxyquinoline;

1-[2S-amino-3-(4-methoxy-2-bromo-6-methylphenyl)-1-oxopropyl]-1,2,3,4-tetrahydro-3-methylquinoline;

1-[2S-amino-3-(4-methoxy-2-bromo-6-methylphenyl)-1-oxopropyl]-2,3-dihydro-1H-indole;

1-[2S-amino-3-(4-methoxy-2-bromo-6-methylphenyl)-1-oxopropyl]-1,2,3,4-tetrahydro-6-methoxyquinoline;

1-[2S-amino-3-(4-(methoxycarbonyl)oxy-2-bromo-6-methylphenyl)-1-oxopropyl]-1,2,3,4-tetrahydro-3-methylquinoline;

1-[2S-amino-3-(4-(methoxycarbonyl)oxy-2-bromo-6-methylphenyl)-1-oxopropyl]-2,3-dihydro-1H-indole;

1-[2S-amino-3-(4-(methoxycarbonyl)oxy-2-bromo-6-methylphenyl)-1-oxopropyl]-1,2,3,4-tetrahydro-6-methoxyquinoline;

1-[2S-amino-3-(4-(ethoxycarbonyl)oxy-2-bromo-6-methylphenyl)-1-oxopropyl]-1,2,3,4-tetrahydro-3-methylquinoline;

1-[2S-amino-3-(4-(ethoxycarbonyl)oxy-2-bromo-6-methylphenyl)-1-oxopropyl]-2,3-dihydro-1H-indole;

1-[2S-amino-3-(4-(ethoxycarbonyl)oxy-2-bromo-6-methylphenyl)-1-oxopropyl]-1,2,3,4-tetrahydro-6-methoxyquinoline;

1-[2S-amino-3-(4-((2-methylpropoxy)carbonyl)oxy-2-bromo-6-methylphenyl)-1-oxopropyl]-1,2,3,4-tetrahydro-3-methylquinoline;

1-[2S-amino-3-(4-((2-methylpropoxy)carbonyl)oxy-2-bromo-6-methylphenyl)-1-oxopropyl]-2,3-dihydro-1H-indole;

1-[2S-amino-3-(4-((2-methylpropoxy)carbonyl)oxy-2-bromo-6-methylphenyl)-1-oxopropyl]-1,2,3,4-tetrahydro-6-methoxyquinoline;

1-[2S-amino-3-(4-((2-propenyloxy)carbonyl)oxy-2-bromo-6-methylphenyl)-1-oxopropyl]-1,2,3,4-tetrahydro-3-methylquinoline;

1-[2S-amino-3-(4-((2-propenyloxy)carbonyl)oxy-2-bromo-6-methylphenyl)-1-oxopropyl]-2,3-dihydro-1H-indole;

1-[2S-amino-3-(4-((2-propenyloxy)carbonyl)oxy-2-bromo-6-methylphenyl)-1-oxopropyl]-1,2,3,4-tetrahydro-6-methoxyquinoline;

1-[2S-amino-3-(4-hydroxy-2-chloro-6-methylphenyl)-1-oxopropyl]-1,2,3,4-tetrahydro-3-methylquinoline;

1-[2S-amino-3-(4-hydroxy-2-chloro-6-methylphenyl)-1-oxopropyl]-2,3-dihydro-1H-indole;

1-[2S-amino-3-(4-hydroxy-2-chloro-6-methylphenyl)-1-oxopropyl]-1,2,3,4-tetrahydro-6-methoxyquinoline;

1-[2S-amino-3-(4-methoxy-2-chloro-6-methylphenyl)-1-oxopropyl]-1,2,3,4-tetrahydro-3-methylquinoline;
1-[2S-amino-3-(4-methoxy-2-chloro-6-methylphenyl)-1-oxopropyl]-2,3-dihydro-1H-indole;
1-[2S-amino-3-(4-methoxy-2-chloro-6-methylphenyl)-1-oxopropyl]-1,2,3,4-tetrahydro-6-methoxyquinoline;
1-[2S-amino-3-(4-(methoxycarbonyl)oxy-2-chloro-6-methylphenyl)-1-oxopropyl]-1,2,3,4-tetrahydro-3-methylquinoline; -
1-[2S-amino-3-(4-(methoxycarbonyl)oxy-2-chloro-6-methylphenyl)-1-oxopropyl]-1-2,3-dihydro-1H-indole;
1-[2S-amino-3-(4-(methoxycarbonyl)oxy-2-chloro-6-methylphenyl)-1-oxopropyl]-1,2,3,4-tetrahydro-6-methoxyquinoline;
1-[2S-amino-3-(4-(ethoxycarbonyl)oxy-2-chloro-6-methylphenyl)-1-oxopropyl]-1,2,3,4-tetrahydro-3-methylquinoline; -
1-[2S-amino-3-(4-(ethoxycarbonyl)oxy-2-chloro-6-methylphenyl)-1-oxopropyl]-2,3-dihydro-1H-indole;
1-[2S-amino-3-(4-(ethoxycarbonyl)oxy-2-chloro-6-methylphenyl)-1-oxopropyl]-1,2,3,4-tetrahydro-6-methoxyquinoline;
1-[2S-amino-3-(4-((2-methylpropoxy)carbonyl)oxy-2-chloro-6-methylphenyl)-1-oxopropyl]-1,2,3,4-tetrahydro-3-methylquinoline;
1-[2S-amino-3-(4-((2-methylpropoxy)carbonyl)oxy-2-chloro-6-methylphenyl)-1-oxopropyl]-2,3-dihydro-1H-indole;
1-[2S-amino-3-(4-((2-methylpropoxy)carbonyl)oxy-2-chloro-6-methylphenyl)-1-oxopropyl]-1,2,3,4-tetrahydro-6-methoxyquinoline;
1-[2S-amino-3-(4-((2-propenyloxy)carbonyl)oxy-2-chloro-6-methylphenyl)-1-oxopropyl]-1,2,3,4-tetrahydro-3-methylquinoline;
1-[2S-amino-3-(4-((2-propenyloxy)carbonyl, oxy-2-chloro-6-methylphenyl)-1-oxopropyl]-2,3-dihydro-1H-indole;
1-[2S-amino-3-(4-((2-propenyloxy)carbonyl)oxy-2-chloro-6-methylphenyl)-1-oxopropyl]-1,2,3,4-tetrahydro-6-methoxyquinoline;
1-[2S-amino-3-(4-hydroxy-2-methylphenyl)-1-oxopropyl]-1,2,3,4-tetrahydro-3-methylquinoline;
1-[2S-amino-3-(4-hydroxy-2-methylphenyl)-1-oxopropyl]-2,3-dihydro-1H-indole;
1-[2S-amino-3-(4-hydroxy-2-methylphenyl)-1-oxopropyl]-1,2,3,4-tetrahydro-8-fluoroquinoline;
1-[2S-amino-3-(4-methoxy-2-methylphenyl)-1-oxopropyl]-1,2,3,4-tetrahydro-3-methylquinoline;
1-[2S-amino-3-(4-methoxy-2-methylphenyl)-1-oxopropyl]-2,3-dihydro-1H-indole;
1-[2S-amino-3-(4-methoxy-2-methylphenyl)-1-oxopropyl]-1,2,3,4-tetrahydro-8-fluoroquinoline;
1-[2S-amino-3-(4-(methoxycarbonyl)oxy-2-methylphenyl)-1-oxopropyl]-1,2,3,4-tetrahydro-3-methylquinoline;
1-[2S-amino-3-(4-(methoxycarbonyl)oxy-2-methylphenyl)-1-oxopropyl]-2,3-dihydro-1H-indole;
1-[2S-amino-3-(4-(methoxycarbonyl)oxy-2-methylphenyl)-1-oxopropyl]-1,2,3,4-tetrahydro-8-fluoroquinoline;
1-[2S-amino-3-(4-(ethoxycarbonyl)oxy-2-methylphenyl)-1-oxopropyl]-1,2,3,4-tetrahydro-3-methylquinoline;
1-[2S-amino-3-(4-(ethoxycarbonyl)oxy-2-methylphenyl)-1-oxopropyl]-2,3-dihydro-1H-indole;
1-[2S-amino-3-(4-(ethoxycarbonyl)oxy-2-methylphenyl)-1-oxopropyl]-1,2,3,4-tetrahydro-8-fluoroquinoline;
1-[2S-amino-3-(4-((2-methylpropoxy)carbonyl)oxy-2-methylphenyl)-1-oxopropyl]-1,2,3,4-tetrahydro-3-methylquinoline;
1-[2S-amino-3-(4-((2-methylpropoxy)carbonyl)oxy-2-methylphenyl)-1-oxopropyl]-2,3-dihydro-1H-indole;
1-[2S-amino-3-(4-((2-methylpropoxy)carbonyl)oxy-2-methylphenyl)-1-oxopropyl]-1,2,3,4-tetrahydro-8-fluoroquinoline;
1-[2S-amino-3-(4-((2-propenyloxy)carbonyl)oxy-2-methylphenyl)-1-oxopropyl]-1,2,3,4-tetrahydro-3-methylquinoline;
1-[2S-amino-3-(4-((2-propenyloxy)carbonyl)oxy-2-methylphenyl)-1-oxopropyl]-2,3-dihydro-1H-indole;
1-[2S-amino-3-(4-((2-propenyloxy)carbonyl)oxy-2-methylphenyl)-1-oxopropyl]-1,2,3,4-tetrahydro-8-fluoroquinoline;
1-[2S-amino-3-(4-hydroxy-2-bromophenyl)-1-oxopropyl]-1,2,3,4-tetrahydro-3-methylquinoline;
1-[2S-amino-3-(4-hydroxy-2-bromophenyl)-1-oxopropyl]-2,3-dihydro-1H-indole;
1-[2S-amino-3-(4-hydroxy-2-bromophenyl)-1-oxopropyl]-1,2,3,4-tetrahydro-8-chloroquinoline;
1-[2S-amino-3-(4-methoxy-2-bromophenyl)-1-oxopropyl]-1,2,3,4-tetrahydro-3-methylquinoline;
1-[2S-amino-3-(4-methoxy-2-bromophenyl)-1-oxopropyl]-2,3-dihydro-1H-indole;
1-[2S-amino-3-(4-methoxy-2-bromophenyl)-1-oxopropyl]-1,2,3,4-tetrahydro-8-chloroquinoline;
1-[2S-amino-3-(4-(methoxycarbonyl)oxy-2-bromophenyl)-1-oxopropyl]-1,2,3,4-tetrahydro-3-methylquinoline;
1-[2S-amino-3-(4-(methoxycarbonyl)oxy-2-bromophenyl)-1-oxopropyl]-2,3-dihydro-1H-indole;
1-[2S-amino-3-(4-(methoxycarbonyl)oxy-2-bromophenyl)-1-oxopropyl]-1,2,3,4-tetrahydro-8-chloroquinoline;
1-[2S-amino-3-(4-(ethoxycarbonyl)oxy-2-bromophenyl)-1-oxopropyl]-1,2,3,4-tetrahydro-3-methylquinoline;
1-[2S-amino-3-(4-(ethoxycarbonyl)oxy-2-bromophenyl)-1-oxopropyl]-2,3-dihydro-1H-indole;
1-[2S-amino-3-(4-(ethoxycarbonyl)oxy-2-bromophenyl)-1-oxopropyl]-1,2,3,4-tetrahydro-8-chloroquinoline;
1-[2S-amino-3-(4-((2-methylpropoxy)carbonyl)oxy-2-bromophenyl)-1-oxopropyl]-1,2,3,4-tetrahydro-3-methylquinoline;
1-[2S-amino-3-(4-((2-methylpropoxy)carbonyl)oxy-2-bromophenyl)-1-oxopropyl]-2,3-dihydro-1H-indole;
1-[2S-amino-3-(4-((2-methylpropoxy)carbonyl)oxy-2-bromophenyl)-1-oxopropyl]-1,2,3,4-tetrahydro-8-chloroquinoline;
1-[2S-amino-3-(4-((2-propenyloxy)carbonyl)oxy-2-bromophenyl)-1-oxopropyl]-1,2,3,4-tetrahydro-3-methylquinoline;
1-[2S-amino-3-(4-((2-propenyloxy)carbonyl)oxy-2-bromophenyl)-1-oxopropyl]-2,3-dihydro-1H-indole;
1-[2S-amino-3-(4-((2-propenyloxy)carbonyl)oxy-2-bromophenyl)-1-oxopropyl]-1,2,3,4-tetrahydro-8-chloroquinoline;
1-[2S-amino-3-(4-hydroxy-2-chlorophenyl)-1-oxopropyl]-1,2,3,4-tetrahydro-3-methylquinoline;
1-[2S-amino-3-(4-hydroxy-2-chlorophenyl)-1-oxopropyl]-2,3-dihydro-1H-indole;
1-[2S-amino-3-(4-hydroxy-2-chlorophenyl)-1-oxopropyl]-1,2,3,4-tetrahydro-8-hydroxyquinoline;
1-[2S-amino-3-(4-methoxy-2-chlorophenyl)-1-oxopropyl]-1,2,3,4-tetrahydro-3-methylquinoline;
1-[2S-amino-3-(4-methoxy-2-chlorophenyl)-1-oxopropyl]-2,3-dihydro-1H-indole;
1-[2S-amino-3-(4-methoxy-2-chlorophenyl)-1-oxopropyl]-1,2,3,4-tetrahydro-8-hydroxyquinoline;
1-[2S-amino-3-(4-(methoxycarbonyl)oxy-2-chlorophenyl)-1-oxopropyl]-1,2,3,4-tetrahydro-3-methylquinoline;
1-[2S-amino-3-(4-(methoxycarbonyl)oxy-2-chlorophenyl)-1-oxopropyl]-2,3-dihydro-1H-indole;

1-[2S-amino-3-(4-(methoxycarbonyl)oxy-2-chlorophenyl)-1-oxopropyl]-1,2,3,4-tetrahydro-8-hydroxyquinoline;
1-[2S-amino-3-(4-(ethoxycarbonyl)oxy-2-chlorophenyl)-1-oxopropyl]-1,2,3,4-tetrahydro-3-methylquinoline;
1-[2S-amino-3-(4-(ethoxycarbonyl)oxy-2-chlorophenyl)-1-oxopropyl]-2,3-dihydro-1H-indole;
1-[2S-amino-3-(4-(ethoxycarbonyl)oxy-2-chlorophenyl)-1-oxopropyl]-1,2,3,4-tetrahydro-8-hydroxyquinoline;
1-[2S-amino-3-(4-((2-methylpropoxy)carbonyl)oxy-2-chlorophenyl)-1-oxopropyl]-1,2,3,4-tetrahydro-3-methylquinoline;
1-[2S-amino-3-(4-((2-methylpropoxy)carbonyl)oxy-2-chlorophenyl)-1-oxopropyl]-2,3-dihydro-1H-indole;
1-[2S-amino-3-(4-((2-methylpropoxy)carbonyl)oxy-2-chlorophenyl)-1-oxopropyl]-1,2,3,4-tetrahydro-8-hydroxyquinoline;
1-[2S-amino-3-(4-((2-propenyloxy)carbonyl)oxy-2-chlorophenyl)-1-oxopropyl]-1,2,3,4-tetrahydro-3-methylquinoline;
1-[2S-amino-3-(4-((2-propenyloxy)carbonyl)oxy-2-chlorophenyl)-1-oxopropyl]-2,3-dihydro-1H-indole;
1-[2S-amino-3-(4-((2-propenyloxy)carbonyl)oxy-2-chlorophenyl)-1-oxopropyl]-1,2,3,4-tetrahydro-8-hydroxyquinoline;
1-[2S-amino-3-(4-hydroxy-2,6-dimethylphenyl)-1-oxopropyl]-1,2,3,4-tetrahydro-8-methoxyquinoline;
1-[2S-amino-3-(4-methoxy-2,6-dimethylphenyl)-1-oxopropyl]-1,2,3,4-tetrahydro-8-methoxyquinoline;
1-[2S-amino-3-(4-(methoxycarbonyl)oxy-2,6-dimethylphenyl)-1-oxopropyl]-1,2,3,4-tetrahydro-8-methoxyquinoline;
1-[2S-amino-3-(4-(ethoxycarbonyl)oxy-2,6-dimethylphenyl)-1-oxopropyl]-1,2,3,4-tetrahydro-8-methoxyquinoline;
1-[2S-amino-3-(4-((2-methylpropoxy)carbonyl)oxy-2,6-dimethylphenyl)-1-oxopropyl]-1,2,3,4-tetrahydro-8-methoxyquinoline;
1-[2S-amino-3-(4-((2-propenyloxy)carbonyl)oxy-2,6-dimethylphenyl)-1-oxopropyl]-1,2,3,4-tetrahydro-8-methoxyquinoline;
1-[2S-amino-3-(4-hydroxy-2,6-dimethylphenyl)-1-oxopropyl]-1,2,3,4-tetrahydroquinoline;
1-[2S-amino-3-(4-methoxy-2,6-dimethylphenyl)-1-oxopropyl]-1,2,3,4-tetrahydroquinoline;
1-[2S-amino-3-(4-(methoxycarbonyl)oxy-2,6-dimethylphenyl)-1-oxopropyl]-1,2,3,4-tetrahydroquinoline;
1-[2S-amino-3-(4-(ethoxycarbonyl)oxy-2,6-dimethylphenyl)-1-oxopropyl]-1,2,3,4-tetrahydroquinoline;
1-[2S-amino-3-(4-((2-methylpropoxy)carbonyl)oxy-2,6-dimethylphenyl)-1-oxopropyl]-1,2,3,4-tetrahydroquinoline;
1-[2S-amino-3-(4-((2-propenyloxy)carbonyl)oxy-2,6-dimethylphenyl)-1-oxopropyl]-1,2,3,4-tetrahydroquinoline;
1-[2R-amino-3-(4-hydroxy-2,6-dimethylphenyl)-1-oxopropyl]-1,2,3,4-tetrahydro-3-methylquinoline;
1-[2R-amino-3-(4-hydroxy-2,6-dimethylphenyl)-1-oxopropyl]-2,3-dihydro-1H-indole;
1-[2R-amino-3-(4-hydroxy-2,6-dimethylphenyl)-1-oxopropyl]-1,2,3,4-tetrahydro-6-methoxyquinoline;
1-[2R-amino-3-(4-methoxy-2,6-dimethylphenyl)-1-oxopropyl]-1,2,3,4-tetrahydro-3-methylquinoline;
1-[2R-amino-3-(4-methoxy-2,6-dimethylphenyl)-1-oxopropyl]-2,3-dihydro-1H-indole;
1-[2R-amino-3-(4-methoxy-2,6-dimethylphenyl)-1-oxopropyl]-1,2,3,4-tetrahydro-6-methoxyquinoline;
1-[2R-amino-3-(4-(methoxycarbonyl)oxy-2,6-dimethylphenyl)-1-oxopropyl]-1,2,3,4-tetrahydro-3-methylquinoline;
1-[2R-amino-3-(4-(methoxycarbonyl)oxy-2,6-dimethylphenyl)-1-oxopropyl]-2,3-dihydro-1H-indole;
1-[2R-amino-3-(4-(methoxycarbonyl)oxy-2,6-dimethylphenyl)-1-oxopropyl]-1,2,3,4-tetrahydro-6-methoxyquinoline;
1-[2R-amino-3-(4-(ethoxycarbonyl)oxy-2,6-dimethylphenyl)-1-oxopropyl]-1,2,3,4-tetrahydro-3-methylquinoline;
1-[2R-amino-3-(4-(ethoxycarbonyl)oxy-2,6-dimethylphenyl)-1-oxopropyl]-2,3-dihydro-1H-indole;
1-[2R-amino-3-(4-(ethoxycarbonyl)oxy-2,6-dimethylphenyl)-1-oxopropyl]-1,2,3,4-tetrahydro-6-methoxyquinoline;
1-[2R-amino-3-(4-((2-methylpropoxy)carbonyl)oxy-2,6-dimethylphenyl)-1-oxopropyl]-1,2,3,4-tetrahydro-3-methylquinoline;
1-[2R-amino-3-(4-((2-methylpropoxy)carbonyl)oxy-2,6-dimethylphenyl)-1-oxopropyl]-2,3-dihydro-1H-indole;
1-[2R-amino-3-(4-((2-methylpropoxy)carbonyl)oxy-2,6-dimethylphenyl)-1-oxopropyl]-1,2,3,4-tetrahydro-6-methoxyquinoline;
1-[2R-amino-3-(4-((2-propenyloxy)carbonyl)oxy-2,6-dimethylphenyl)-1-oxopropyl]-1,2,3,4-tetrahydro-3-methylquinoline;
1-[2R-amino-3-(4-((2-propenyloxy)carbonyl)oxy-2,6-dimethylphenyl)-1-oxopropyl]-2,3-dihydro-1H-indole;
1-[2R-amino-3-(4-((2-propenyloxy)carbonyl)oxy-2,6-dimethylphenyl)-1-oxopropyl]-1,2,3,4-tetrahydro-6-methoxyquinoline;
1-[2R-amino-3-(4-hydroxy-2-bromo-6-methylphenyl)-1-oxopropyl]-1,2,3,4-tetrahydro-3-methylquinoline;
1-[2R-amino-3-(4-hydroxy-2-bromo-6-methylphenyl)-1-oxopropyl]-2,3-dihydro-1H-indole;
1-[2R-amino-3-(4-hydroxy-2-bromo-6-methylphenyl)-1-oxopropyl]-1,2,3,4-tetrahydro-6-methoxyquinoline;
1-[2R-amino-3-(4-methoxy-2-bromo-6-methylphenyl)-1-oxopropyl]-1,2,3,4-tetrahydro-3-methylquinoline;
1-[2R-amino-3-(4-methoxy-2-bromo-6-methylphenyl)-1-oxopropyl]-2,3-dihydro-1H-indole;
1-[2R-amino-3-(4-methoxy-2-bromo-6-methylphenyl)-1-oxopropyl]-1,2,3,4-tetrahydro-6-methoxyquinoline;
1-[2R-amino-3-(4-(methoxycarbonyl)oxy-2-bromo-6-methylphenyl)-1-oxopropyl]-1,2,3,4-tetrahydro-3-methylquinoline;
1-[2R-amino-3-(4-(methoxycarbonyl)oxy-2-bromo-6-methylphenyl)-1-oxopropyl]-2,3-dihydro-1H-indole;
1-[2R-amino-3-(4-(methoxycarbonyl)oxy-2-bromo-6-methylphenyl)-1-oxopropyl]-1,2,3,4-tetrahydro-6-methoxyquinoline;
1-[2R-amino-3-(4-(ethoxycarbonyl)oxy-2-bromo-6-methylphenyl)-1-oxopropyl]-1,2,3,4-tetrahydro-3-methylquinoline;
1-[2R-amino-3-(4-(ethoxycarbonyl)oxy-2-bromo-6-methylphenyl)-1-oxopropyl]-2,3-dihydro-1H-indole;
1-[2R-amino-3-(4-(ethoxycarbonyl)oxy-2-bromo-6-methylphenyl)-1-oxopropyl]-1,2,3,4-tetrahydro-6-methoxyquinoline;
1-[2R-amino-3-(4-((2-methylpropoxy)carbonyl)oxy-2-bromo-6-methylphenyl)-1-oxopropyl]-1,2,3,4-tetrahydro-3-methylquinoline;
1-[2R-amino-3-(4-((2-methylpropoxy)carbonyl)oxy-2-bromo-6-methylphenyl)-1-oxopropyl]-2,3-dihydro-1H-indole;
1-[2R-amino-3-(4-((2-methylpropoxy)carbonyl)oxy-2-bromo-6-methylphenyl)-1-oxopropyl]-1,2,3,4-tetrahydro-6-methoxyquinoline;

1-[2R-amino-3-(4-((2-propenyloxy)carbonyl)oxy-2-bromo-6-methylphenyl)-1-oxopropyl]-1,2,3,4-tetrahydro-3-methylquinoline;
1-[2R-amino-3-(4-((2-propenyloxy)carbonyl)oxy-2-bromo-6-methylphenyl)-1-oxopropyl]-2,3-dihydro-1H-indole;
1-[2R-amino-3-(4-((2-propenyloxy)carbonyl)oxy-2-bromo-6-methylphenyl)-1-oxopropyl]-1,2,3,4-tetrahydro-6-methoxyquinoline;
1-[2R-amino-3-(4-hydroxy-2-chloro-6-methylphenyl)-1-oxopropyl]-1,2,3,4-tetrahydro-3-methylquinoline;
1-[2R-amino-3-(4-hydroxy-2-chloro-6-methylphenyl)-1-oxopropyl]-2,3-dihydro-1H-indole;
1-[2R-amino-3-(4-hydroxy-2-chloro-6-methylphenyl)-1-oxopropyl]-1,2,3,4-tetrahydro-6-methoxyquinoline;
1-[2R-amino-3-(4-methoxy-2-chloro-6-methylphenyl)-1-oxopropyl]-1,2,3,4-tetrahydro-3-methylquinoline;
1-[2R-amino-3-(4-methoxy-2-chloro-6-methylphenyl)-1-oxopropyl]-2,3-dihydro-1H-indole;
1-[2R-amino-3-(4-methoxy-2-chloro-6-methylphenyl)-1-oxopropyl]-1,2,3,4-tetrahydro-6-methoxyquinoline;
1-[2R-amino-3-(4-(methoxycarbonyl)oxy-2-chloro-6-methylphenyl)-1-oxopropyl]-1,2,3,4-tetrahydro-3-methylquinoline;
1-[2R-amino-3-(4-(methoxycarbonyl)oxy-2-chloro-6-methylphenyl)-1-oxopropyl]-2,3-dihydro-1H-indole;
1-[2R-amino-3-(4-(methoxycarbonyl)oxy-2-chloro-6-methylphenyl)-1-oxopropyl]-1,2,3,4-tetrahydro-6-methoxyquinoline;
1-[2R-amino-3-(4-(ethoxycarbonyl)oxy-2-chloro-6-methylphenyl)-1-oxopropyl]-1,2,3,4-tetrahydro-3-methylquinoline;
1-[2R-amino-3-(4-(ethoxycarbonyl)oxy-2-chloro-6-methylphenyl)-1-oxopropyl]-2,3-dihydro-1H-indole;
1-[2R-amino-3-(4-(ethoxycarbonyl)oxy-2-chloro-6-methylphenyl)-1-oxopropyl]-1,2,3,4-tetrahydro-6-methoxyquinoline;
1-[2R-amino-3-(4-((2-methylpropoxy)carbonyl)oxy-2-chloro-6-methylphenyl)-1-oxopropyl]-1,2,3,4-tetrahydro-3-methylquinoline;
1-[2R-amino-3-(4-((2-methylpropoxy)carbonyl)oxy-2-chloro-6-methylphenyl)-1-oxopropyl]-2,3-dihydro-1H-indole;
1-[2R-amino-3-(4-((2-methylpropoxy)carbonyl)oxy-2-chloro-6-methylphenyl)-1-oxopropyl]-1,2,3,4-tetrahydro-6-methoxyquinoline;
1-[2R-amino-3-(4-((2-propenyloxy)carbonyl)oxy-2-chloro-6-methylphenyl)-1-oxopropyl]-1,2,3,4-tetrahydro-3-methylquinoline;
1-[2R-amino-3-(4-((2-propenyloxy)carbonyl)oxy-2-chloro-6-methylphenyl)-1-oxopropyl]-2,3-dihydro-1H-indole;
1-[2R-amino-3-(4-((2-propenyloxy)carbonyl)oxy-2-chloro-6-methylphenyl)-1-oxopropyl]-1,2,3,4-tetrahydro-6-methoxyquinoline;
1-[2R-amino-3-(4-hydroxy-2-methylphenyl)-1-oxopropyl]-1,2,3,4-tetrahydro-3-methylquinoline;
1-[2R-amino-3-(4-hydroxy-2-methylphenyl)-1-oxopropyl]-2,3-dihydro-1H-indole;
1-[2R-amino-3-(4-hydroxy-2-methylphenyl)-1-oxopropyl]-1,2,3,4-tetrahydro-8-fluoroquinoline;
1-[2R-amino-3-(4-methoxy-2-methylphenyl)-1-oxopropyl]-1,2,3,4-tetrahydro-3-methylquinoline;
1-[2R-amino-3-(4-methoxy-2-methylphenyl)-1-oxopropyl]-2,3-dihydro-1H-indole;
1-[2R-amino-3-(4-methoxy-2-methylphenyl)-1-oxopropyl]-1,2,3,4-tetrahydro-8-fluoroquinoline;
1-[2R-amino-3-(4-(methoxycarbonyl)oxy-2-methylphenyl)-1-oxopropyl]-1,2,3,4-tetrahydro-3-methylquinoline;
1-[2R-amino-3-(4-(methoxycarbonyl)oxy-2-methylphenyl)-1-oxopropyl]-2,3-dihydro-1H-indole;
1-[2R-amino-3-(4-(methoxycarbonyl)oxy-2-methylphenyl)-1-oxopropyl]-1,2,3,4-tetrahydro-8-fluoroquinoline;
1-[2R-amino-3-(4-(ethoxycarbonyl)oxy-2-methylphenyl)-1-oxopropyl]-1,2,3,4-tetrahydro-3-methylquinoline;
1-[2R-amino-3-(4-(ethoxycarbonyl)oxy-2-methylphenyl)-1-oxopropyl]-2,3-dihydro-1H-indole;
1-[2R-amino-3-(4-(ethoxycarbonyl)oxy-2-methylphenyl)-1-oxopropyl]-1,2,3,4-tetrahydro-8-fluoroquinoline;
1-[2R-amino-3-(4-((2-methylpropoxy)carbonyl)oxy-2-methylphenyl)-1-oxopropyl]-1,2,3,4-tetrahydro-3-methylquinoline;
1-[2R-amino-3-(4-((2-methylpropoxy)carbonyl)oxy-2-methylphenyl)-1-oxopropyl]-2,3-dihydro-1H-indole;
1-[2R-amino-3-(4-((2-methylpropoxy)carbonyl)oxy-2-methylphenyl)-1-oxopropyl]-1,2,3,4-tetrahydro-8-fluoroquinoline;
1-[2R-amino-3-(4-((2-propenyloxy)carbonyl)oxy-2-methylphenyl)-1-oxopropyl]-1,2,3,4-tetrahydro-3-methylquinoline;
1-[2R-amino-3-(4-((2-propenyloxy)carbonyl)oxy-2-methylphenyl)-1-oxopropyl]-2,3-dihydro-1H-indole;
1-[2R-amino-3-(4-((2-propenyloxy)carbonyl)oxy-2-methylphenyl)-1-oxopropyl]-1,2,3,4-tetrahydro-8-fluoroquinoline;
1-[2R-amino-3-(4-hydroxy-2-bromophenyl)-1-oxopropyl]-1,2,3,4-tetrahydro-3-methylquinoline;
1-[2R-amino-3-(4-hydroxy-2-bromophenyl)-1-oxopropyl]-2,3-dihydro-1H-indole;
1-[2R-amino-3-(4-hydroxy-2-bromophenyl)-1-oxopropyl]-1,2,3,4-tetrahydro-8-chloroquinoline;
1-[2R-amino-3-(4-methoxy-2-bromophenyl)-1-oxopropyl]-1,2,3,4-tetrahydro-3-methylquinoline;
1-[2R-amino-3-(4-methoxy-2-bromophenyl)-1-oxopropyl]-2,3-dihydro-1H-indole;
1-[2R-amino-3-(4-methoxy-2-bromophenyl)-1-oxopropyl]-1,2,3,4-tetrahydro-8-chloroquinoline;
1-[2R-amino-3-(4-(methoxycarbonyl)oxy-2-bromophenyl)-1-oxopropyl]-1,2,3,4-tetrahydro-3-methylquinoline;
1-[2R-amino-3-(4-(methoxycarbonyl)oxy-2-bromophenyl)-1-oxopropyl]-2,3-dihydro-1H-indole;
1-[2R-amino-3-(4-(methoxycarbonyl)oxy-2-bromophenyl)-1-oxopropyl]-1,2,3,4-tetrahydro-8-chloroquinoline;
1-[2R-amino-3-(4-(ethoxycarbonyl)oxy-2-bromophenyl)-1-oxopropyl]-1,2,3,4-tetrahydro-3-methylquinoline;
1-[2R-amino-3-(4-(ethoxycarbonyl)oxy-2-bromophenyl)-1-oxopropyl]-2,3-dihydro-1H-indole;
1-[2R-amino-3-(4-(ethoxycarbonyl)oxy-2-bromophenyl)-1-oxopropyl]-1,2,3,4-tetrahydro-8-chloroquinoline;
1-[2R-amino-3-(4-((2-methylpropoxy)carbonyl)oxy-2-bromophenyl)-1-oxopropyl]-1,2,3,4-tetrahydro-3-methylquinoline;
1-[2R-amino-3-(4-((2-methylpropoxy)carbonyl)oxy-2-bromophenyl)-1-oxopropyl]-2,3-dihydro-1H-indole;
1-[2R-amino-3-(4-((2-methylpropoxy)carbonyl)oxy-2-bromophenyl)-1-oxopropyl]-1,2,3,4-tetrahydro-8-chloroquinoline;
1-[2R-amino-3-(4-((2-propenyloxy)carbonyl)oxy-2-bromophenyl)-1-oxopropyl]-1,2,3,4-tetrahydro-3-methylquinoline;
1-[2R-amino-3-(4-((2-propenyloxy)carbonyl)oxy-2-bromophenyl)-1-oxopropyl]-2,3-dihydro-1H-indole;
1-[2R-amino-3-(4-((2-propenyloxy)carbonyl)oxy-2-bromophenyl)-1-oxopropyl]-1,2,3,4-tetrahydro-8-chloroquinoline;
1-[2R-amino-3-(4-hydroxy-2-chlorophenyl)-1-oxopropyl]-1,2,3,4-tetrahydro-3-methylquinoline;

1-[2R-amino-3-(4-hydroxy-2-chlorophenyl)-1-oxopropyl]-2,3-dihydro-1H-indole;

1-[2R-amino-3-(4-hydroxy-2-chlorophenyl)-1-oxopropyl]-1,2,3,4-tetrahydro-8-hydroxyquinoline;

1-[2R-amino-3-(4-methoxy-2-chlorophenyl)-1-oxopropyl]-1,2,3,4-tetrahydro-3-methylquinoline;

1-[2R-amino-3-(4-methoxy-2-chlorophenyl)-1-oxopropyl]-2,3-dihydro-1H-indole;

1-[2R-amino-3-(4-methoxy-2-chlorophenyl)-1-oxopropyl]-1,2,3,4-tetrahydro-8-hydroxyquinoline;

1-[2R-amino-3-(4-(methoxycarbonyl)oxy-2-chlorophenyl)-1-oxopropyl]-1,2,3,4-tetrahydro-3-methylquinoline;

1-[2R-amino-3-(4-(methoxycarbonyl)oxy-2-chlorophenyl)-1-oxopropyl]-2,3-dihydro-1H-indole;

1-[2R-amino-3-(4-(methoxycarbonyl)oxy-2-chlorophenyl)-1-oxopropyl]-1,2,3,4-tetrahydro-8-hydroxyquinoline;

1-[2R-amino-3-(4-(ethoxycarbonyl)oxy-2-chlorophenyl)-1-oxopropyl]-1,2,3,4-tetrahydro-3-methylquinoline;

1-[2R-amino-3-(4-(ethoxycarbonyl)oxy-2-chlorophenyl)-1-oxopropyl]-2,3-dihydro-1H-indole;

1-[2R-amino-3-(4-(ethoxycarbonyl)oxy-2-chlorophenyl)-1-oxopropyl]-1,2,3,4-tetrahydro-8-hydroxyquinoline;

1-[2R-amino-3-(4-((2-methylpropoxy)carbonyl)oxy-2-chlorophenyl)-1-oxopropyl]-1,2,3,4-tetrahydro-3-methylquinoline;

1-[2R-amino-3-(4-((2-methylpropoxy)carbonyl)oxy-2-chlorophenyl)-1-oxopropyl]-2,3-dihydro-1H-indole;

1-[2R-amino-3-(4-((2-methylpropoxy)carbonyl)oxy-2-chlorophenyl)-1-oxopropyl]-1,2,3,4-tetrahydro-8-hydroxyquinoline;

1-[2R-amino-3-(4-((2-propenyloxy)carbonyl)oxy-2-chlorophenyl)-1-oxopropyl]-1,2,3,4-tetrahydro-3-methylquinoline;

1-[2R-amino-3-(4-((2-propenyloxy)carbonyl)oxy-2-chlorophenyl)-1-oxopropyl]-2,3-dihydro-1H-indole;

1-[2R-amino-3-(4-((2-propenyloxy)carbonyl)oxy-2-chlorophenyl)-1-oxopropyl]-1,2,3,4-tetrahydro-8-hydroxyquinoline;

1-[2R-amino-3-(4-hydroxy-2,6-dimethylphenyl)-1-oxopropyl]-1,2,3,4-tetrahydro-8-methoxyquinoline;

1-[2R-amino-3-(4-methoxy-2,6-dimethylphenyl)-1-oxopropyl]-1,2,3,4-tetrahydro-8-methoxyquinoline;

1-[2R-amino-3-(4-(methoxycarbonyl)oxy-2,6-dimethylphenyl)-1-oxopropyl]-1,2,3,4-tetrahydro-8-methoxyquinoline;

1-[2R-amino-3-(4-(ethoxycarbonyl)oxy-2,6-dimethylphenyl)-1-oxopropyl]-1,2,3,4-tetrahydro-8-methoxyquinoline;

1-[2R-amino-3-(4-((2-methylpropoxy)carbonyl)oxy-2,6-dimethylphenyl)-1-oxopropyl]-1,2,3,4-tetrahydro-8-methoxyquinoline;

1-[2R-amino-3-(4-((2-propenyloxy)carbonyl)oxy-2,6-dimethylphenyl)-1-oxopropyl]-1,2,3,4-tetrahydro-8-methoxyquinoline;

1-[2R-amino-3-(4-hydroxy-2,6-dimethylphenyl)-1-oxopropyl]-1,2,3,4-tetrahydroquinoline;

1-[2R-amino-3-(4-methoxy-2,6-dimethylphenyl)-1-oxopropyl]-1,2,3,4-tetrahydroquinoline;

1-[2R-amino-3-(4-(methoxycarbonyl)oxy-2,6-dimethylphenyl)-1-oxopropyl]-1,2,3,4-tetrahydroquinoline;

1-[2R-amino-3-(4-(ethoxycarbonyl)oxy-2,6-dimethylphenyl)-1-oxopropyl]-1,2,3,4-tetrahydroquinoline;

1-[2R-amino-3-(4-((2-methylpropoxy)carbonyl)oxy-2,6-dimethylphenyl)-1-oxopropyl]-1,2,3,4-tetrahydroquinoline;

1-[2R-amino-3-(4-((2-propenyloxy)carbonyl)oxy-2,6-dimethylphenyl)-1-oxopropyl]-1,2,3,4-tetrahydroquinoline;

A most highly preferred family of specific compounds within Formula IV consists of compounds, and tautomers and enantiomers thereof, as well as the pharmaceutically-acceptable salts and esters thereof, as follows:

1-[2S-amino-3-(4-hydroxyphenyl)-1-oxopropyl]-1,2,3,4-tetrahydroquinoline;

1-[2S-amino-3-(4-hydroxy-2-methylphenyl)-1-oxopropyl]-1,2,3,4-tetrahydroquinoline;

1-[2S-amino-3-(4-hydroxy-2,6-dimethylphenyl)-1-oxopropyl]-1,2,3,4-tetrahydroquinoline;

1-[2R-amino-3-(4-hydroxy-2,6-dimethylphenyl)-1-oxopropyl]-1,2,3,4-tetrahydroquinoline;

1-[2S-amino-3-(4-hydroxy-2,6-dimethylphenyl)-1-oxopropyl]-1,2,3,4-tetrahydro-3-methylquinoline;

1-[2S-amino-3-(4-hydroxy-2,6-dimethylphenyl)-1-oxopropyl]-2,3-dihydro-1H-indole;

1-[2S-amino-3-(4-hydroxy-2,6-dimethylphenyl)-1-oxopropyl]-1,2,3,4-tetrahydro-6-methoxyquinoline;

1-[2S-amino-3-(4-methoxy-2,6-dimethylphenyl)-1-oxopropyl]-1,2,3,4-tetrahydroquinoline;

1-[2S-amino-3-(4-hydroxy-2,6-dimethylphenyl)-1-oxopropyl]-1,2,3,4-tetrahydro-8-hydroxyquinoline; and 5-[2S-amino-3-(4-hydroxy-2,6-dimethylphenyl)-1-oxopropyl]-5,6,11,12-tetrahydrodibenz[b,f]azocine.

The term "hydrido" denotes a single hydrogen atom (H). This hydrido group may be attached, for example, to a oxygen atom to form a hydroxyl group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formulas I–IV are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I–IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formulas I–IV include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I–IV by reacting, for example, the appropriate acid or base with the compound of Formulas I–IV.

Compounds of general Formulas I–IV can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzyoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formulas I–IV with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formulas I–IV can likewise be obtained by utilizing optically active starting materials. These isomers may be in the form of a free acid, a free base, an ester or a salt.

General Synthetic Procedures

Compounds embraced by Formulas I–IV may be prepared in accordance with Scheme I. A suitably protected amino acid with a free carboxyl group is treated by appropriate activating agents in order to form an amide with the appropriate aromatic amine. The preferred amino protecting group for the amino acid is the N-t-butyloxycarbonyl (BOC) group, but other protecting groups, such as the N-carbobenzoxy function are also feasible. The preferred activation process is the "mixed anhydride" reaction series, as depicted, but other condensing agents such as the various carbodiimides are also successful.

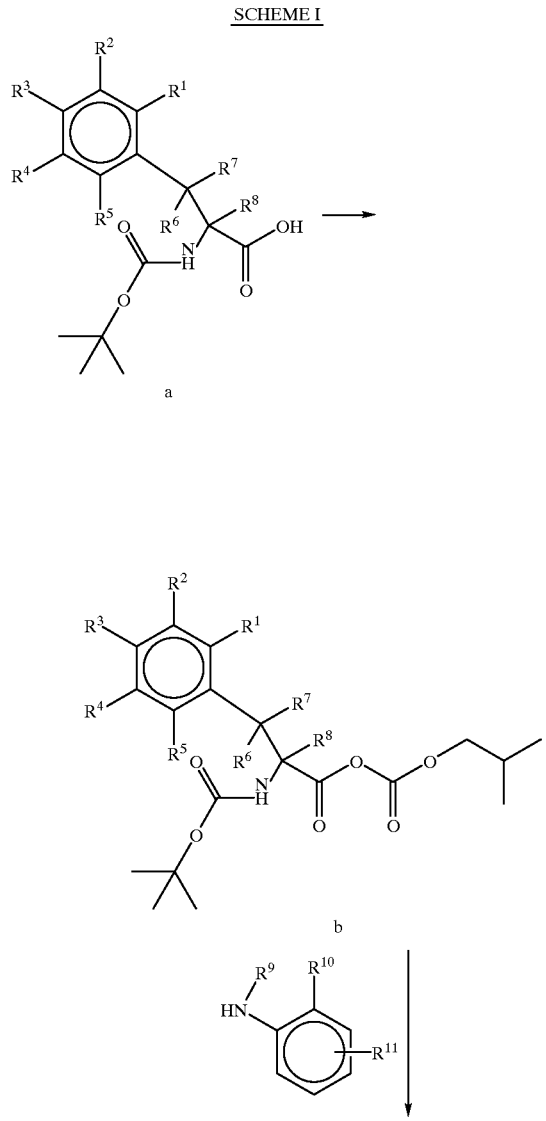

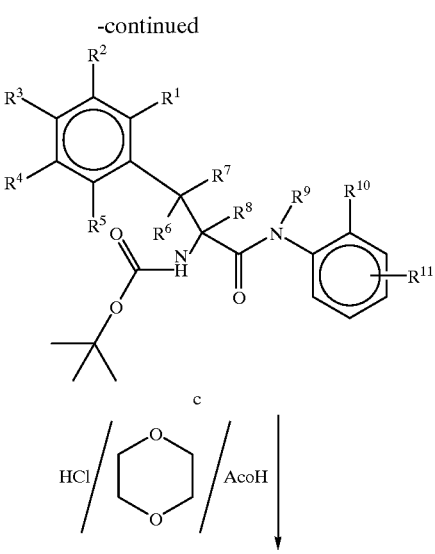

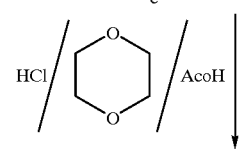

As shown in Scheme I, BOC-protected amino acid a is dissolved in a suitable solvent such as methylene chloride, methylene chloride-N,N-dimethylformamide (DMF), neat DMF, tetrahydrofuran (THF), or a combination of these or similar non-protic solvents. The solution is cooled to between 0° and −40° C., and 5A molecular sieves are introduced. This is followed by the addition of a slight excess of suitable non-protic base, such as a tertiary amine. N-methylmorpholine is particularly preferred. This mixture is stirred under nitrogen for 10 min to 1 hr. All further reaction steps are also run under nitrogen. The reaction mixture is then cooled to −50° C. to −70° C., and one equivalent of isobutylchloroformate is added. A water ice bath cooled with methanol is then used to bring the reaction temperature to ca. −5° C., where it is maintained for 30–60 min., giving the intermediate mixed anhydride b. The reaction mixture is then recooled to −50° C. to −70° C., and a slight excess of the appropriate amine is added, either neat or dissolved or suspended in a solvent such as DMF or methylene chloride. The cold bath is then removed and the mixture allowed to come to ambient temperature. After 6–24 hrs. of stirring, the reaction mixture is filtered, the residue is washed, and filtrate and wash-combined and extracted with 0.5 N KHSO$_4$. The aqueous phase is washed with methylene chloride, the organic phases are combined and dried (MgSO$_4$ or Na$_2$SO$_4$), solvent is removed, and the product c is purified by silica gel column chromatography if necessary. The BOC protecting group is then removed by treatment with HCl in dioxane, acetic acid, methanol, or some combination thereof, affording the HCl salt of the target compound d.

The following Examples 1–12 are detailed descriptions of the methods of preparation of compounds of Formulas I–IV. These detailed preparations fall within the scope of, and serve to exemplify, the above-described Generic Procedures which form part of the invention. These Examples 1–12 are presented for illustrative purposes only and are not intended as a restriction on the scope of the invention. All parts are by weight and temperatures are expressed in Centigrade degrees unless otherwise indicated. Most of the commercially-available starting materials were obtained from Aldrich Chemical Co., Milwaukee, Wis.

EXAMPLE 1

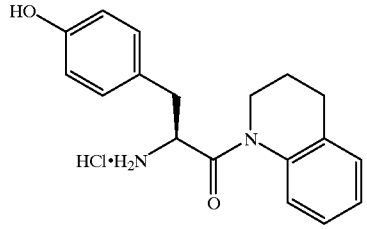

1-[2S-amino-3-(4-hydroxyphenyl)-1-oxopropyl]-1,2,3,4-tetrahydroquinoline, monohydrochloride A 1 L round-bottom-3-necked flask was fitted with a magnetic stirrer, an inlet for dry nitrogen gas, a stopper, and a Y-tube which contained a thermometer and a drying tube outlet. N-t-BOC-(L)-tyrosine (15 g, 53.32 mmol) was charged into the flask, as was 10 g molecular sieves (5A, 8–12 mesh beads). Dichloromethane (300 mL) and N,N-dimethylformamide (DMF) (100 mL) were added, the nitrogen was turned on, and the mixture was cooled to –40° (dry ice-acetone bath). N-methylmorpholine (6.74 mL, 6.20 g, 61.32 mmol) was added, and the mixture was stirred for 40 min. The reaction temperature was then lowered to –60°, and isobutylchloroformate (7.33 mL, 7.65 g, 55.99 mmol) was added. The cold bath was changed to ice-methanol, and the reaction temperature was allowed to rise to –5° over 1 hr. The reaction mixture was then recooled to –60°, and 1,2,3,4-tetrahydroquinoline (8.03 mL, 8.52 g, 63.99 mmol) dissolved in DMF (90 mL) was added. The cold bath was removed and the reaction mixture was allowed to come to room temperature. The mixture was stirred under nitrogen for 18 hr, and then filtered to remove sieves and N-methylmorpholine hydrochloride. The solid was washed twice with dichloromethane, and the combined filtrates were washed with 0.5 M potassium bisulfate solution (200 mL). The aqueous phase was washed with fresh dichloromethane, and the combined organic phases were dried (MgSO$_4$), filtered, and evaporated at reduced pressure, finally with an oil pump vacuum source. The temperature was kept at or below 35°. The resultant syrup was applied to a column of silica gel, and eluted with ethyl acetate-hexane mixtures, giving the N-t-BOC derivative of the title compound.

The N-t-BOC derivative of the title compound (2 g) was dissolved in glacial acetic acid (20 mL). HCl in dioxane (6.4N, 2 mL) was added, and the mixture stirred (lightly stoppered) for 3 hr. The reaction mixture was evaporated at reduced pressure, finally with a vacuum pump (bath temperature did not exceed 35°). The resulting oil was triturated with ether, filtered, dried in a vacuum oven (30° with a nitrogen sweep), and finally dried in an abderhalden apparatus (77°) overnight, giving the title compound as the hydrated hydrochloride: $C_{18}H_{20}N_2O_2 \cdot HCl \cdot 0.25\ H_2O$, mw 337.32. Calc C, 64.09; H, 6.42; N, 8.30, Cl, 10.51. Found C, 64.16; H, 6.36; N, 8.24; Cl, 10.51. $\alpha_D$+146°, $\alpha_{365\ nm}$+734°, nmr: arom. multiplets centered at δ=3.05, 4.10.

EXAMPLE 2

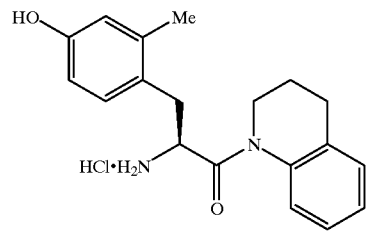

1-[2S-amino-3-(4-hydroxy-2-methylphenyl)-1-oxopropyl]-1,2,3,4-tetrahydroquinoline, monohydrochloride BOC-(L)-2-methyltyrosine was reacted with 1,2,3,4-tetrahydroquinoline in a mixed anhydride coupling by the method of Example 1, giving, after deprotection of the N-t-BOC group, as also described in Example 1, the title compound as the hydrated hydrochloride: $C_{19}H_{22}N_2O_2 \cdot HCl \cdot 0.5\ H_2O$, mw 355.85. Calc C, 64.13; H, 6.80; N, 7.87; Cl, 9.96. Found C, 64.17; H, 6.66; N, 7.91; Cl, 9.90. $\alpha_D$+171°, $\alpha_{365\ nm}$+840°, nmr: arom. methyl δ=1.6 s.

EXAMPLE 3

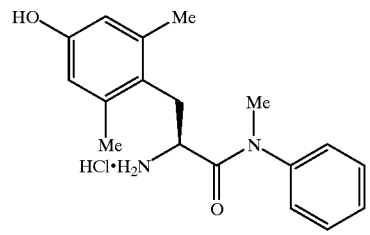

αS-amino-4-hydroxy-N,2,6-trimethyl-N-phenylbenzenepropanamide, monohydrochloride BOC-(L)2,6-dimethyltyrosine was reacted as described in Example 1, except that N-methylaniline replaced the tetrahydroquinoline. The title compound was isolated as the hydrated hydrochloride: $C_{18}H_{22}N_2O_2 \cdot HCl \cdot 0.25\ H_2O$, mw 339.34. Calc C, 63.71; H, 6.98; N, 8.26; Cl, 10.45. Found C, 63.34; H, 6.84; N, 8.19; Cl, 10.19. $\alpha_D$+140°, $\alpha_{365\ nm}$+679°, nmr: arom. methyls δ=1.80 s, tyrosyl arom. protons δ=6.36 s, N-methyl δ=3.09 s, N-phenyl protons δ=7.15–7.40 m.

EXAMPLE 4

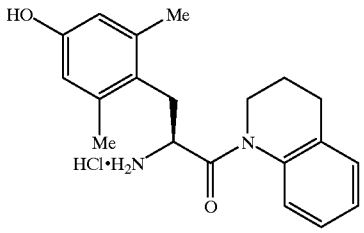

1-[2S-amino-3-(4-hydroxy-2,6-dimethylphenyl)-1-oxopropyl]-1,2,3,4-tetrahydroquinoline, monohydrochloride A 250 mL round-bottom-3-necked flask was fitted with a magnetic stirrer, an inlet for dry nitrogen gas, a stopper, and a Y-tube which contained a thermometer and a drying tube outlet. N-t-BOC-L-2,6-dimethyltyrosine (4.0 g, 12.9 mmol) was charged into the flask, as was 7 g molecular sieves (5A, 8–12 mesh beads). Dichloromethane (75 mL) and N,N-dimethylformamide (DMF) (50 mL) were added, the nitrogen was turned on, and the mixture was cooled to −40° (dry ice-acteone bath). N-methylmorpholine (1.68 mL, 1.50 g, 14.87 mmol) was added, and the mixture was stirred for 40 min. The reaction temperature was then lowered to −60°, and isobutylchloroformate (1.78 mL, 1.85 g, 13.6 mmol) was added. The cold bath was changed to ice-methanol, and the reaction temperature was allowed to rise to −5° over 1 hr. The reaction mixture was then recooled to −60°, and 1,2,3,4-tetrahydroquinoline (1.87 mL, 1.98 g, 14.9 mmol) dissolved in DMF (20 mL) was added. The cold bath was removed and the reaction mixture was allowed to come to room temperature. The mixture was stirred under nitrogen for 18 hr, and then filtered to remove sieves and N-methylmorpholine hydrochloride. The solid was washed twice with dichloromethane, and the combined filtrates were washed with 0.5 M potassium bisulfate solution (100 mL). The aqueous phase was washed with fresh dichloromethane, and the combined organic phases were dried (MgSO$_4$), filtered, and evaporated at reduced pressure, finally with an oil pump vacuum source. The temperature was kept at or below 35°. The resultant syrup was applied to a column of silica gel, and eluted with ethyl acetate-hexane mixtures, giving the N-t-BOC derivative of the title compound.

The N-t-BOC derivative of the title compound (1.2 g) was dissolved in glacial acetic acid (3 mL). HCl in dioxane (6.4N, 1 mL) was added, and the mixture stirred (lightly stoppered) for 3 hr. The solution was filtered and diluted with 200 mL of diethyl ether. The resultant solid was washed with ether and dried (35° C.) in vacuo. The solid was treated with 5 mL of water. The resulting solid was dried (33° C.) in vacuo, giving the title compound as the hydrated hydrochloride: $C_{20}H_{24}N_2O_2 \cdot 0.5H_2O$, mw 369.89. Cal C, 64.94; H, 7.09; N, 7.57; Cl 9.58. Found C, 64.81; H, 7.05; N, 7.24; Cl, 9.44. $\alpha_D$+150°, $\alpha_{365\,nm}$+690°, nmr: arom. methyl δ=1.80 br.s., tyrosyl arom. protons δ=6.21 s, tetrahydroquinoline arom. protons δ=7.0–7.2 m.

EXAMPLE 5

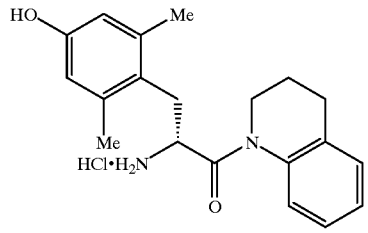

1-[2R-amino-3-(4-hydroxy-2,6-dimethylphenyl)-1-oxopropyl]-1,2,3,4-tetrahydroquinoline, monohydrochloride BOC-(D)-2,6-dimethyltyrosine was reacted as described in Example 1. The title compound was isolated as the anhydrous hydrochloride: $C_{20}H_{24}N_2O_2 \cdot HCl$, mw 360.88. Calc C, 66.56; H, 6.98; N, 7.76; Cl 9.82. Found C, 66.24; H, 7.05; N, 7.70; Cl, 9.77.

$\alpha_D$ −202°, $\alpha_{365}$−946°, nmr: arom, methyl δ1.80 br.s., tyrosyl arom. protons δ=6.22 s, tetrahydroquinoline arom. protons δ=7.0–7.2 m.

EXAMPLE 6

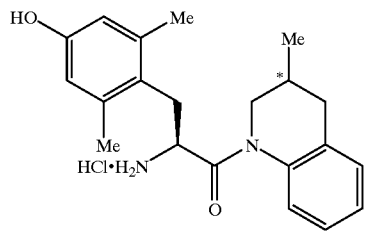

Diastereomer A

1-[-2S-amino-3-(4-hydroxy-2,6-dimethlyphenyl)-1-oxopropyl]-1,2,3,4-tetrahydro-3-methylquinoline, hydrochloride BOC-(L)-2,6-dimethyltyrosine was reacted with racemic 3-methyl-1,2,3,4-tetrahydroquinoline hydrochloride by the method of Example 1. One equivalent of N-methylmorpholine was added to a suspension of amine hydrochloride suspension in dimethyl formamide (DMF), before the addition to the mixed anhydride. The silica gel column chromatography separated the diastereomeric pair, with the first diastereomer emerging being labeled Diastereomer A. The last diastereomer emerging, Diastereomer B, will be further described in Example 7. Diastereomer A was treated with HCl-dioxane and glacial acetic acid by the method of Example 1, to give the title compound as the hydrated hydrochloride: $C_{21}H_{26}N_2O_2 \cdot 0.875$ HCl·0.5 H$_2$O, mw 379.34. Calc C, 66.49; H, 7.41; N, 7.38; Cl, 8.18. Found C, 66.38; H, 7.22; N, 7.15; Cl, 8.31. $\alpha_D$+191°, $\alpha_{365\,nm}$+862°, nmr: tetrahydroquinoline methyl δ=0.90d (trace containment Example 13 visible at δ=0.7), arom. methyl δ=1.75 s, tyrosyl arom. protons δ=6.21s.

EXAMPLE 7

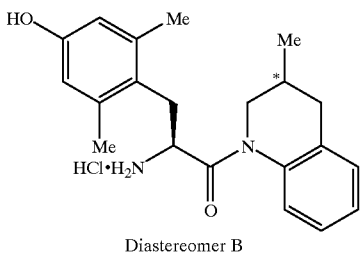

Diastereomer B

1-[2S-amino-3-(4-hydroxy-2,6-dimethylphenyl)-1-oxopropyl]-1,2,3,4-tetrahydro-3-methylquinoline, hydrochloride The slower diastereomer emerging from the silica gel column described in Example 6 was Diastereomer B. It was treated with HCl-dioxane and glacial acetic acid as described in Example 1, to give the title compound as the hydrated hydrochloride: $C_{21}H_{26}N_2O_2 \cdot 0.875HCl \cdot 0.875 H_2O$, mw 381.60. Calc C, 66.09; H, 7.43; N, 7.34; Cl, 8.13. Found C, 65.73; H, 7.18; N, 7.09; Cl, 8.52. $\alpha_D+195°$, $\alpha_{365\ nm}$ 936°, nmr: tetrahydroquinoline methyl $\delta=0.72d$ (trace contaminant Example 12 visible at $\delta=0.90$), arom. methyl $\delta 1.78s$, tyrosyl arom. protons $\delta=6.21s$.

EXAMPLE 8

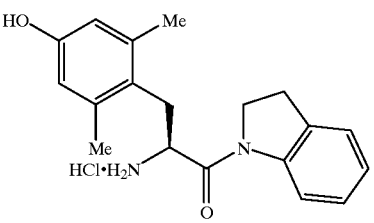

1-[2S-amino-3-(4-hydroxy-2,6-dimethylphenyl)-1-oxopropyl]-2,3-dihydro-1H-indole, monohydrochloride BOC-(L)-2,6-dimethyltyrosine was reacted as described in Example 1, except that indoline replaced the tetrahydroquinoline. The title compound was isolated as the anhydrous hydrochloride: $C_{19}H_{22}N_2O_2 \cdot HCl$, mw 346.86. Calc C, 65.79; H, 6.68; N, 8.08; Cl, 10.22. Found C, 65.48; H, 6.75; N, 8.06; Cl 10.11. $\alpha_D+274°$, $\alpha_{365}+1296°$, nmr: arom. methyls $\delta=2.15s$, tyrosyl arom. protons $\delta=6.40s$, indoline arom protons $\delta 7.0$–$7.25$ two triplets.

EXAMPLE 9

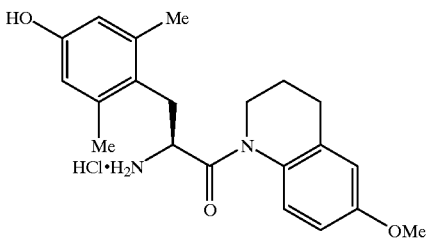

1-[2S-amino-3-(4-hydroxy-2,6-dimethylphenyl)-1-oxopropyl]-1,2,3,4-tetrahydro-6-methoxyquinoline, monohydrochloride BOC-(L)-2,6-dimethyltyrosine was reacted as described in Example 6, except that 6-methoxy-1,2,3,4-tetrahydroquinoline hydrochloride replaced the 3-methyl 1,2,3,4-tetrahydroquinoline hydrochloride. The title compound was isolated as the anhydrous hydrochloride: $C_{21}H_{26}N_2O_3 \cdot HCl$, mw 390.91. Calc C, 64.52; H, 6.96; N, 7.17; Cl, 9.07. Found C, 64.43; H, 6.98; N, 7.26; Cl, 9.14. $\alpha_D+149°$, $\alpha_{365\ nm}+749°$, nmr: methoxy $\delta=3.72s$, arom. methyls $\delta=1.81$ br.s.

EXAMPLE 10

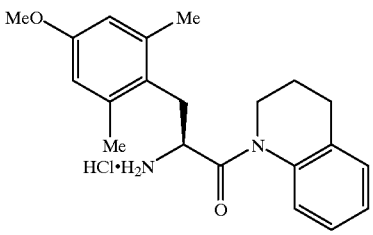

1-[2S-amino-3-(4-methoxy-2,6-dimethylphenyl)-1-oxopropyl]-1,2,3,4-tetrahydroquinoline, monohydrochloride The BOC-protected derivative of the title compound of Example 4 (2.0 g, 4.71 mmol) was treated with sodium hydride (50% dispersion in mineral oil, 0.25 g, 5.18 mmol, pre-washed with hexane before reaction) in DMF (50 mL) for 30 min. Methyl iodide (0.87 g, 0.38 ml, 6.12 mmol) was added and the mixture was stirred under a drying tube for 16 hr. The reaction mixture was then partitioned between water and ether. The aqueous phase was washed with ether, the organic phases were then combined, dried ($MgSO_4$), filtered, and dried in vacuo to give a syrup which was applied to a silica gel column. The desired material was eluted with ethyl acetate-hexane mixtures, and, after removal of solvent, was treated with dioxane-HCl and glacial acetic acid as described in Example 1, giving the title compound as the anhydrous hydrochloride: $C_{21}H_{26}N_2O_2 \cdot HCl$, mw 374.91. Calc C, 67.28; H, 7.26; N, 7.47, ; Cl, 9.46. Found C, 66.96; H, 7.44; N, 7.32; Cl, 9.28. $\alpha_D+198°$, $\alpha_{365\ nm}$ 30 927°, nmr: methoxy $\delta=3.41s$, arom. methyls $\delta=1.82s$, tyrosyl arom. protons $\delta=6.40$.

EXAMPLE 11

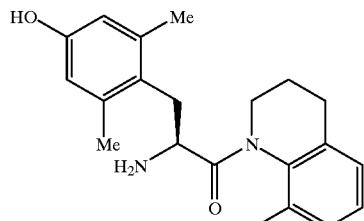

1-[2S-amino-3-(4-hydroxy-2,6-dimethylphenyl)-1-oxopropyl]-1,2,3,4-tetrahydro-8-hydroxyquinoline, monohydrochloride BOC-(L)-2,6-dimethyltyrosine was reacted as described in Example 6, except that 8-hydroxy-1,2,3,4-tetrahydroquinoline hydrochloride replaced the 3-methyl 1,2,3,4-tetrahydroquinoline hydrochloride. The title compound was isolated as the hydrated hydrochloride: $C_{20}H_{24}N_2O_3 \cdot HCl \cdot 0.5 H_2O$, mw 385.88. Calc C, 62.25; H, 6.79; N, 7.26; Cl, 9.19. Found C, 62.44; H, 6.64; N, 7.28; Cl, 9.13. $\alpha_D+110°$, $\alpha_{365\ nm}$ 30 485°, nmr: arom. methyls δ=1.80s, tyrosine arom. protons δ=6.23s, tetrahydroquinoline arom. protons δ=6.52d, 6.80d, 7.01t.

EXAMPLE 12

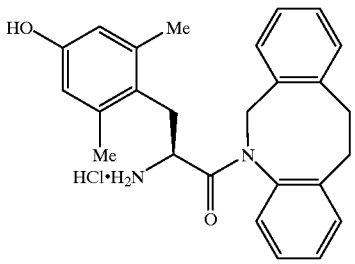

5-[2S-amino-3-(4-hydroxy-2,6-dimethylphenyl)-1-oxopropyl]-5,6,11,12-tetrahydrodibenz[b,f]azocine, monohydrochloride BOC-(L)-2,6 dimethyltyrosine was reacted as described in Example 6, except that dibenz[b,f]-azocine hydrochloride replaced the 3-methyl 1,2,3,4-tetrahydroquinoline hydrochloride. The title compound was isolated as the hydrated hydrochloride: $C_{26}H_{28}N_2O_2 \cdot HCl \cdot 0.5\ H_2O$, mw 445.99. Calc C, 70.02; H, 6.78; N, 6.28; Cl, 7.95. Found C, 70.06; H, 6.72; N, 6.28; Cl, 8.28. αD+97°, $\alpha_{365\ nm}+411°$, nmr: arom. methyls δ=1.60s, 1.88s; tyrosyl aromatic protons δ=6.20s, 6.45s.

Biological Evaluation

Prevention of the neurodegenerative consequences associated with conditions of hypoxia or ischemia in a mammalian subject may be accomplished by administration of a compound of Formula I to the subject. For example, compounds of the invention have been evaluated in biological assays to measure the inhibition of hypoxia- or ischemia-induced neuronal toxicity. Compounds of the invention, as well as some earlier-known PCP agonist compounds, were evaluated by various in vivo and in vitro assays to determine compound activity as an NMDA antagonist or PCP agonist. These biological assays, described below, included a radioreceptor assay, a forebrain ischemia assay and a behavioral assay.

Radioreceptor Assay

Compounds 1–12 of Examples 1–12, respectively, were compared against PCP and TCP in an assay to determine the relative potency of the compounds interacting with PCP receptors. To determine the effect of the compounds in a PCP receptor assay, crude membrane preparations were prepared by homogenizing whole rat brains in 30 ml of ice-cold 5 mM Tris-HCl, pH 7.4 (Tris buffer), with a Brinkman Polytron (setting 6, 15 sec). The homogenate was centrifuged twice at 20,000×g for 15 min at 4° C. with an intervening resuspension of the pellet in cold Tris buffer. The final pellet was resuspended in Tris buffer to obtain a final concentration of 0.1 g of tissue per ml. Incubation tubes were prepared in triplicate and contained 0.1 ml of tissue suspension, 1 nM of $^3$H-TCP and varying concentrations of displacing ligand (0.1–30,000 nM) in a final volume of 0.5 ml. After a 1 hour incubation, the contents of the test tubes were filtered through Schleier & Schuell #32 filters, which had been presoaked for at least 2 hours in 0.05% polyethyleneimine. The test tubes were rinsed twice and the filters once with 4 ml of tris buffer. Radioactivity on the filters was determined by liquid scintillation spectrometry. Specific binding was defined as the total amount of tritiated compound bound minus the amount bound in the presence of 10 μM of TCP compound. $K_i$ values were determined using the method of Cheng & Prusoff [*Biochem. Pharmacol.*, 22, 3099–3108 (1973)]. Results are shown in Table I, below.

TABLE I

| Test Compound | $K_i$ apparent (nM) |
| --- | --- |
| PCP | 96 |
| TCP | 20 |
| Compound No. 1 | 7,100 |
| Compound No. 2 | 800 |
| Compound No. 3 | 2,600 |
| Compound No. 4 | 16 |
| Compound No. 5 | 100 |
| Compound No. 6 | 240 |
| Compound No. 7 | 880 |
| Compound No. 8 | 1,450 |
| Compound No. 9 | 4,100 |
| Compound No. 10 | 4,500 |
| Compound No. 11 | 420 |
| Compound No. 12 | 20,000 |

Forebrain Ischemia Assay

Male Mongolian gerbils, 50–70 gm, were used as subjects. Compound No. 4 (30 mg/kg) was injected i.p. 30 minutes prior to carotid occlusion into 6 gerbils. In preparation for surgical procedures, the animals were lightly anesthetized with methoxyflurane and placed upside down on a heated pad with the animal's snout within a nosecone. A mixture of 70 parts nitrous oxide, 30 parts oxygen and 0.5 part halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow was occluded. Flow was occluded for 4–5 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following the ischemic insult, damaged neurons have been cleared away by glia and the extent of damage can be ascertained within the vulnerable CA1 region of the hippocampus. The cell loss in CA1 was rated as 0 (no loss), 1 (unilateral damage), 2 (bilateral partial cell loss), or 3 (complete bilateral cell loss). The test animals were compared to a group of 69 saline injected gerbils. The groups were compared by Mann-Whitney U test [*Elementary Applied Statistics* (New York: Wiley and Sons), 1965]. The cell loss was significantly reduced in the gerbils given Compound No. 4 (p<0.005).

Behavioral Assay

Compound No. 4 was tested by an in vivo assay which determined stereotypic behavior in rats treated with the compound. Male Sprague-Dawley rats weighing 200 to 250 g were used in the behavioral experiments. Each rat was used only once. Rats were anesthetized lightly with ether before a 20-gauge needle was used to make a hole in the rat's skull for i.c.v. injection of drugs at a later date. These rats were allowed to recover for at least 1 day before being used in the behavioral assays. On the day of the experiement, rats were placed individually into plastic rat cages and allowed at least 1 hr to acclimate before testing. Drugs were administered to rats in a random, single-blind fashion. Behavioral ratings were taken at 5-min intervals up to 1 hr after drug administration (i.p.) using the PCP rating scale as described by Sturgeon et al [Sturgeon, R. D., Fessler, R. G. and Meltzer, H. Y., "Behavioral Rating Scales for Accessing Phencyclidine-Induced Locomotor Activity. Sterotyped Behavior And Ataxia in Rats", *European J. Pharmacol.*, 59, 169 (1970)]. The rating scale for stereotyped behavior is: 0, inactive or nonrepetitive activity; 1, sniffing, grooming or rearing; 2, nondirectional movements, and occasional reciprocal forepaw treading; 3, circling or head-weaving behavior or backpeddling; 4, rapid and continuous circling or head-weaving behavior, assuming a praying posture or gagging; and 5, dyskinetic extension and flexion of limbs, head and neck or head-weaving greater than in "4". Dose-response curves for each treatment were determined at the time of maximal behavioral effect. Peak effects of PCP (2.0–32 mg/kg) after i.p. administration were observed at 15 min. A rating of 5 in the PCP-rating scale was considered as complete stereotyped behavior, that is, a 100% response. At least 21 rats (at least seven rats/dose) were used to determine each dose-response curve and $ED_{50}$ values. $ED_{50}$ values and dose-response curves were evaluated using a computerized Finney assay [*Statistical Methods in Biological Assays,* 2nd Edn., Hatner Pub. Co., New York (1964)]. The ability of the Compound No. 4 to induce stereotyped behavior was assessed at 2.5, 5 and 10 minutes and thereafter every 5 min up to 1 hr after i.p. administration. It was found that Compound No. 4 induced stereotyped behavior at an $ED_{50}$ of 11 mg/kg.

Also embraced within this invention is a class of pharmaceutical compositions comprising one or more compounds of Formulas I–IV in association with one or more non-toxic, pharmaceutically-acceptable carriers and/or diluents and/or adjuvants (collectively referred to herein as "carrier" materials) and, if desired, other active ingredients. The compounds of the present invention may be administered to a mammalian subject, such as a human subject, by any suitable route, preferably in the form of a pharmaceutical composition adapted to such a route, and in a dose effective for the treatment intended. Therapeutically-effective doses of the compounds of the present invention required to prevent or arrest the progress of the medical condition are readily ascertained by one of ordinary skill in the art. The compounds and composition may, for example, be administered by various routes including oral, nasal, topical, buccal and sublingual, or by parenteral administration such as subcutaneous, intramuscular, intravenous and intradermal routes.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula I:

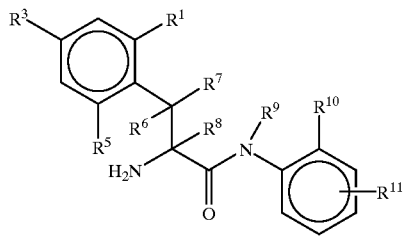

(I)

wherein each of $R^1$, $R^5$, $R^6$, $R^7$, $R^8$, and $R^{11}$ is independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, alkanoyl and amino and amido radicals of the formula

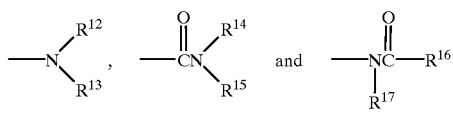

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, aralkyl and aryl;

wherein $R^3$ is selected from hydroxy, alkyl, cycloalkyl, cycloalkylalkyl, haloalkyl, aryl, aralkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, aryl, aralkyl, hydroxyalkyl, alkoxyalkyl, alkoxycarbonyl and alkanoyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

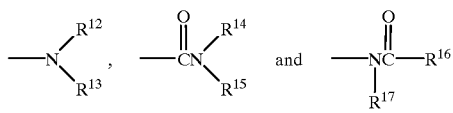

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, alkanoyl, mercapto, alkylthio, arylthio, alkylsulfinyl, arylsulfinyl, alkylsulfonyl, arylsulfonyl, and amino radicals of the formula

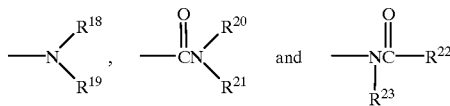

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, aralkyl and aryl;

or a tautomer or an enantiomer thereof, or a pharmaceutically-acceptable ester or salt thereof.

2. Compound of claim 1 wherein each of $R^1$, $R^5$, $R^6$, $R^7$, $R^8$ and $R^{11}$ is independently selected from hydrido, alkyl, cycloalkyl, cycloalkylalkyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, alkanoyl, and amino and amido radicals of the formula

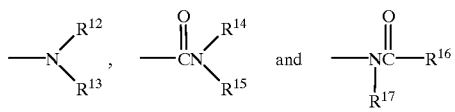

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, phenalkyl and phenyl;

wherein $R^3$ is selected from hydroxy, alkyl, cycloalkyl, cycloalkylalkyl, haloalkyl, phenyl, phenalkyl, hydroxyalkyl, alkoxyalkyl, alkoxycarbonyl alkenylalkyloxycarbonyloxy, alkoxycarbonyloxy, acyl and alkanoyl;

wherein $R^9$ is selected from alkyl, cycloalkyl, cycloalkylalkyl, haloalkyl, phenyl, phenalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

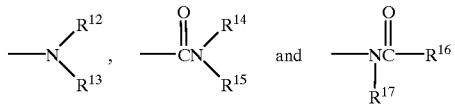

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, cyano, cyanoamino, alkanoyl, and amino and amido radicals of the formula

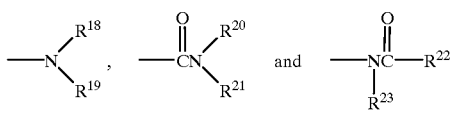

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, phenalkyl and phenyl;

or a tautomer or an enantiomer thereof, or a pharmaceutically-acceptable ester or salt thereof.

3. Compound of claim 2 wherein each of $R^1$, $R^5$, $R^6$, $R^7$, $R^8$ and $R^9$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

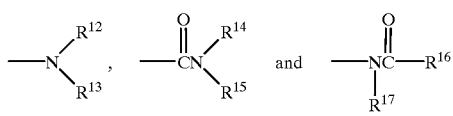

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

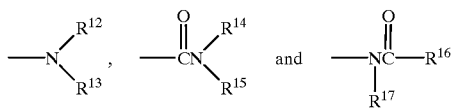

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl and amino and amido radicals of the formula

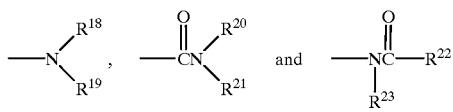

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

4. Compound of claim 3 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

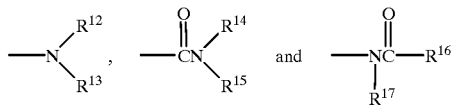

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^7$ is selected from alkyl, cycloalkyl, cycloalkylalkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

wherein $R^{10}$ and $R^{11}$ may be taken together to form a fused aromatic ring; wherein said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl, and amino and amido radicals of the formula

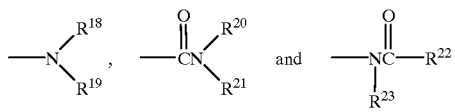

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

5. Compound of claim 4 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein each of $R^6$, $R^7$ and $R^8$ is independently selected from hydrido, alkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

or a tautomer or enantiomer thereof, or a pharmaceutically-acceptable ester or salt thereof.

6. Compound of claim 5 wherein each of $R^1$, $R^5$, $R^{10}$ and $R^{11}$ is independently selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxymethyl, hydroxyethyl, hydroxypropyl, methoxy, ethoxy, propoxy, methoxymethyl, ethoxymethyl and ethoxyethyl;

wherein $R^3$ is selected from hydroxy, methoxy, ethoxy, methoxycarbonyloxy, ethoxycarbonyloxy, (2-methylpropoxy)carbonyloxy and (2-propenyloxy)carbonyloxy;

wherein each of $R^6$, $R^7$ and $R^8$ is hydrido;

$R^9$ is selected from methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, hydroxyethyl, hydroxypropyl and ethoxyethyl;

or a tautomer or an enantiomer thereof, or a pharmaceutically-acceptable ester or salt thereof.

7. Compound of claim 6 which is αS-amino-4-hydroxy-N,2,6-trimethyl-N-phenylbenzenepropanamide, monohydrochloride.

8. A pharmaceutical composition comprising a therapeutically-effective amount of an active compound and a pharmaceutically-acceptable carrier or diluent, said active compound selected from a family of compounds of Formula I:

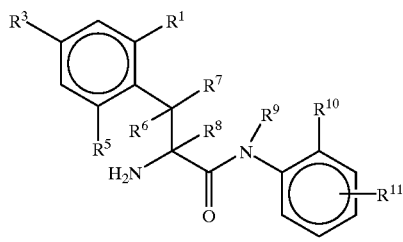

(I)

wherein each of $R^1$, $R^5$, $R^6$, $R^7$, $R^8$, and $R^{11}$ is independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, alkanoyl and amino and amido radicals of the formula

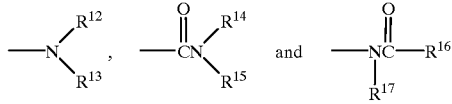

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, aralkyl and aryl;

wherein $R^3$ is selected from hydroxy, alkyl, cycloalkyl, cycloalkylalkyl, haloalkyl, aryl, aralkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, aryl, aralkyl, hydroxyalkyl, alkoxyalkyl, alkoxycarbonyl and alkanoyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

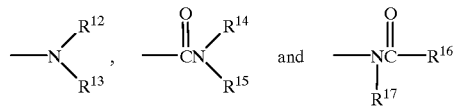

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, alkanoyl, mercapto, alkylthio, arylthio, alkylsulfinyl, arylsulfinyl, alkylsulfonyl, arylsulfonyl, and amino and amido radicals of the formula

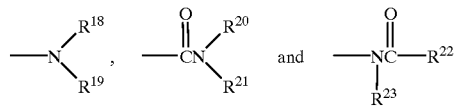

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, aralkyl and aryl;

or a tautomer or an enantiomer thereof, or a pharmaceutically-acceptable ester or salt thereof.

9. The composition of claim 8 wherein each of $R^1$, $R^5$, $R^6$, $R^7$, $R^8$ and $R^{11}$ is independently selected from hydrido, alkyl, cycloalkyl, cycloalkylalkyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, alkanoyl, and amino and amido radicals of the formula

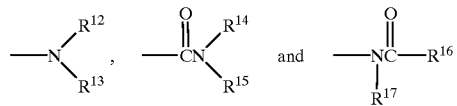

wherein each of $R^{12}$, $R^{13}$, $R^{14}$, $R^{15}$, $R^{16}$ and $R^{17}$ is independently selected from alkyl, cycloalkyl, hydroxyalkyl, cycloalkylalkyl, alkoxyalkyl, phenalkyl and phenyl;

wherein $R^3$ is selected from hydroxy, alkyl, cycloalkyl, cycloalkylalkyl, haloalkyl, phenyl, phenalkyl, hydroxyalkyl, alkoxyalkyl, alkoxycarbonyl alkenylalkyloxycarbonyloxy, alkoxycarbonyloxy, acyl and alkanoyl;

wherein $R^9$ is selected from alkyl, cycloalkyl, cycloalkylalkyl, haloalkyl, phenyl, phenalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

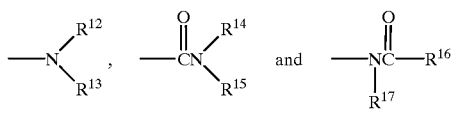

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, cyano, cyanoamino, alkanoyl, and amino and amido radicals of the formula

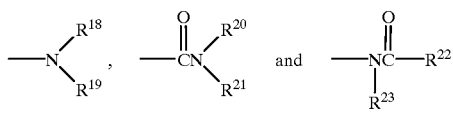

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, phenalkyl and phenyl;

or a tautomer or an enantiomer thereof, or a pharmaceutically-acceptable ester or salt thereof.

10. The composition of claim 9 wherein each of $R^1$, $R^5$, $R^6$, $R^7$, $R^8$ and $R^9$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

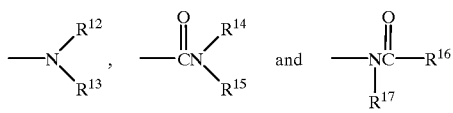

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

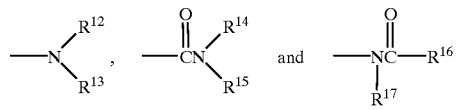

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted at a substituable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl and amino and amido radicals of the formula

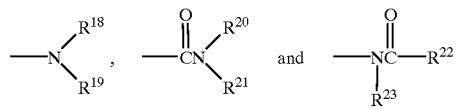

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

11. The composition of claim 10 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

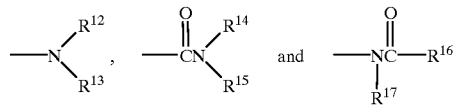

wherein each of $R^{12}$, $R^{13}$, $R^{14}$, $Rl^5$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^7$ is selected from alkyl, cycloalkyl, cycloalkylalkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

wherein $R^{10}$ and $R^{11}$ may be taken together to form a fused aromatic ring; wherein said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl, and amino and amido radicals of the formula

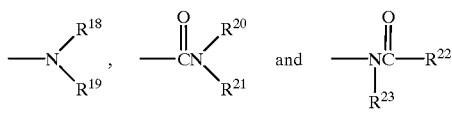

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

12. The composition of claim 11 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein each of $R^6$, $R^7$ and $R^8$ is independently selected from hydrido, alkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

or a tautomer or enantiomer thereof, or a pharmaceutically-acceptable ester or salt thereof.

13. The composition of claim 12 wherein each of $R^1$, $R^5$, $R^{10}$ and $R^{11}$ is independently selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxymethyl, hydroxyethyl, hydroxypropyl, methoxy, ethoxy, propoxy, methoxymethyl, ethoxymethyl and ethoxyethyl;

wherein $R^3$ is selected from hydroxy, methoxy, ethoxy, methoxycarbonyloxy, ethoxycarbonyloxy, (2-methylpropoxy)carbonyloxy and (2-propenyloxy)carbonyloxy;

wherein each of $R^6$, $R^7$ and $R^8$ is hydrido;

$R^9$ is selected from methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, hydroxyethyl, hydroxypropyl and ethoxyethyl;

or a tautomer or an enantiomer thereof, or a pharmaceutically-acceptable ester or salt thereof.

14. The composition of claim 13 wherein said active compound is αS-amino-4-hydroxy-N-2,6-trimethyl-N-phenylbenzenepropanamide, monohydrochloride.

15. A method to treat neurotoxic injury in a subject, which method comprises treating a subject susceptible to or afflicted with neurotoxic injury with a therapeutically effective amount of a compound of Formula I:

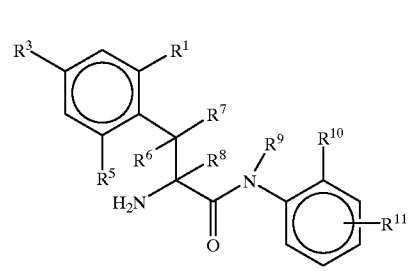

wherein each of $R^1$, $R^5$, $R^6$, $R^7$, $R^8$, and $R^{11}$ is independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, alkanoyl and amino and amido radicals of the formula

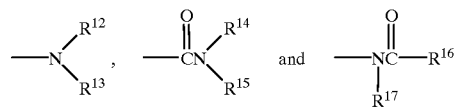

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, aralkyl and aryl;

wherein $R^3$ is selected from hydroxy, alkyl, cycloalkyl, cycloalkylalkyl, haloalkyl, aryl, aralkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, aryl, aralkyl, hydroxyalkyl, alkoxyalkyl, alkoxycarbonyl and alkanoyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

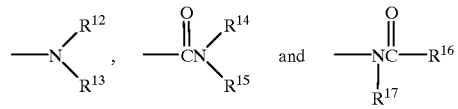

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, alkanoyl, mercapto, alkylthio, arylthio, alkylsulfinyl, arylsulfinyl, alkylsulfonyl, arylsulfonyl, and amino and amido radicals of the formula

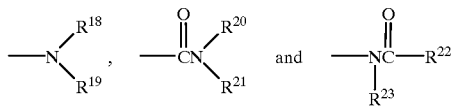

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, aralkyl and aryl;

or a tautomer or an enantiomer thereof, or a pharmaceutically-acceptable ester or salt thereof.

16. The method of claim 15 wherein each of $R^1$, $R^5$, $R^6$, $R^7$, $R^8$ and $R^{11}$ is independently selected from hydrido, alkyl, cycloalkyl, cycloalkylalkyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, alkanoyl, and amino and amido radicals of the formula

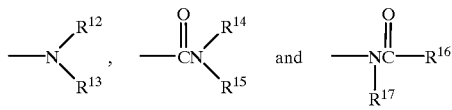

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, alkoxyalkyl, phenalkyl and phenyl;

wherein $R^3$ is selected from hydroxy, alkyl, cycloalkyl, cycloalkylalkyl, haloalkyl, phenyl, phenalkyl, hydroxyalkyl, alkoxyalkyl, alkoxycarbonyl alkenylalkyloxycarbonyloxy, alkoxycarbonyloxy, acyl and alkanoyl;

wherein $R^9$ is selected from alkyl, cycloalkyl, cycloalkylalkyl, haloalkyl, phenyl, phenalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

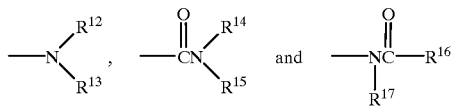

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted with one or more groups selected from alkyl, cycloalkyl, cycloalkylalkyl, carboxyl, oxo, halo, haloalkyl, alkenyl, phenyl, phenalkyl, hydroxy, hydroxyalkyl, alkoxy, phenoxy, alkoxyalkyl, alkoxycarbonyl, phenalkoxy, cyano, cyanoamino, alkanoyl, and amino and amido radicals of the formula

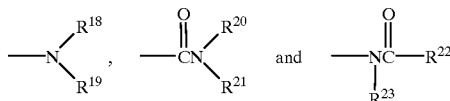

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl, alkoxyalkyl, phenalkyl and phenyl;

or a tautomer or an enantiomer thereof, or a pharmaceutically-acceptable ester or salt thereof.

17. The method of claim 16 wherein each of $R^1$, $R^5$, $R^6$, $R^7$, $R^8$ and $R^9$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

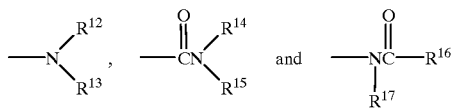

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^9$ is selected from alkyl, cycloalkyl, cycloalkylalkyl, haloalkyl, hydroxyalkyl and alkoxyalkyl;

wherein $R^{10}$ is selected from hydrido, halo, alkyl, cycloalkyl, cycloalkylalkyl, haloalkyl, hydroxy, hydroxyalkyl, alkoxy, aryloxy, alkoxyalkyl, and amino and amido radicals of the formula

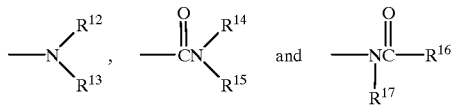

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl, and alkoxyalkyl;

wherein $R^{10}$ and $R^{11}$ may be taken together to form a fused aromatic ring; and wherein said fused aromatic ring may be substituted at a substituable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl and amino and amido radicals of the formula

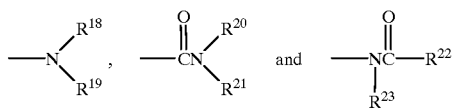

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

18. The method of claim 17 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy, alkoxyalkyl, and amino and amido radicals of the formula

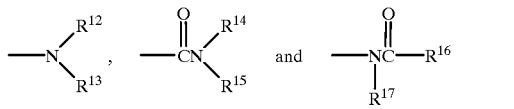

wherein each of $R^{12}$, $R^{13}$, $R^{14}$, $R^{15}$, $R^{16}$ and $R^{17}$ is independently selected from hydrido, alkyl, cycloalkyl, hydroxyalkyl, cycloalkylalkyl and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein $R^7$ is selected from alkyl, cycloalkyl, cycloalkylalkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

wherein $R^{10}$ and $R^{11}$ may be taken together to form a fused aromatic ring; wherein said fused aromatic ring may be substituted at a substitutable position with one or more groups selected from alkyl, cycloalkyl, cycloalkylalkyl, carboxyl, haloalkyl, phenalkyl, hydroxy, hydroxyalkyl, alkoxy, alkoxyalkyl, alkoxycarbonyl, and amino and amido radicals of the formula

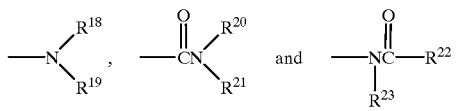

wherein each of $R^{18}$, $R^{19}$, $R^{20}$, $R^{21}$, $R^{22}$ and $R^{23}$ is independently selected from hydrido, alkyl, cycloalkyl, hydroxyalkyl, cycloalkylalkyl and alkoxyalkyl;

or a tautomer or an enantiomer thereof, or a pharmaceutically-acceptable ester or salt thereof.

19. The method of claim 18 wherein each of $R^1$, $R^5$, $R^{10}$ and $R^{11}$ is independently selected from hydrido, halo, alkyl, cycloalkyl, cycloalkylalkyl, haloalkyl, hydroxy, hydroxyalkyl, alkoxy and alkoxyalkyl;

wherein $R^3$ is selected from hydroxy, alkyl, cycloalkyl, cycloalkylalkyl, haloalkyl, phenalkyl, hydroxyalkyl, alkoxyalkyl, alkoxycarbonyl, alkenylalkyloxycarbonyloxy, alkoxycarbonyloxy, acyl and alkanoyl;

wherein each of $R^6$, $R^7$ and $R^8$ is independently selected from hydrido, alkyl, haloalkyl, hydroxyalkyl and alkoxyalkyl;

wherein $R^9$ is selected from alkyl, cycloalkyl, cycloalkylalkyl, haloalkyl, hydroxyalkyl and alkoxyalkyl;

or a tautomer or enantiomer thereof, or a pharmaceutically-acceptable ester or salt thereof.

20. The method of claim 19 wherein each of $R^1$, $R^5$, $R^{10}$ and $R^{11}$ is independently selected from hydrido, chloro, bromo, methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, trifluoromethyl, hydroxymethyl, hydroxyethyl, hydroxypropyl, methoxy, ethoxy, propoxy, methoxymethyl, ethoxymethyl and ethoxyethyl;

wherein $R^3$ is selected from hydroxy, methoxy, ethoxy, methoxycarbonyloxy, ethoxycarbonyloxy, (2-methylpropoxy)carbonyloxy and (2-propenyloxy)carbonyloxy;

wherein each of $R^6$, $R^7$ an $R^8$ is hydrido;

$R^9$ is selected from methyl, ethyl, n-propyl, isopropyl, n-butyl, isobutyl, sec-butyl, tert-butyl, n-pentyl, cyclopropyl, cyclobutyl, cyclopentyl, cyclohexyl, cycloheptyl, hydroxyethyl, hydroxypropyl and ethoxyethyl;

or a tautomer or an enantiomer thereof, or a pharmaceutically-acceptable ester or salt thereof.

21. The method of claim 20 wherein said active compound is αS-amino-4-hydroxy-N-2,6-trimethyl-N-phenylbenzenepropanamide, monohydrochloride.

22. The method of claim 15 wherein said subject is susceptible to or afflicted with a neurodegenerative disease or neurotoxic injury.

23. The method of claim 22 wherein said neurotoxic injury is related to a condition arising from hypoxia, anoxia or ischemia.

24. The method of claim 23 wherein said neurotoxic injury is related to or arises from cerebral ischemia.

* * * * *